United States Patent
Merchant et al.

(10) Patent No.: US 12,383,557 B2
(45) Date of Patent: Aug. 12, 2025

(54) TREATMENT OF CANCER USING COMBINATION THERAPIES COMPRISING GDC-6036 AND GDC-0077

(71) Applicant: Genentech, Inc., South San Francisco, CA (US)

(72) Inventors: Mark Andrew Merchant, Redwood City, CA (US); Jennifer Lee Schutzman, Belmont, CA (US); Zhen Shi, Belmont, CA (US); Chunyan Song, Redwood City, CA (US); Neekesh Vijay Dharia, Burlingame, CA (US); Stephanie Royer Joo, San Diego, CA (US)

(73) Assignee: Genentech, Inc., South San Francisco, CA (US)

( * ) Notice: Subject to any disclaimer, the term of this patent is extended or adjusted under 35 U.S.C. 154(b) by 104 days.

(21) Appl. No.: 18/295,550

(22) Filed: Apr. 4, 2023

(65) Prior Publication Data
US 2023/0321102 A1    Oct. 12, 2023

Related U.S. Application Data

(60) Provisional application No. 63/328,149, filed on Apr. 6, 2022.

(51) Int. Cl.
| | | |
|---|---|---|
| *A61K 31/517* | (2006.01) | |
| *A61K 9/00* | (2006.01) | |
| *A61K 9/16* | (2006.01) | |
| *A61K 31/553* | (2006.01) | |
| *A61P 35/00* | (2006.01) | |

(52) U.S. Cl.
CPC .......... *A61K 31/517* (2013.01); *A61K 9/0053* (2013.01); *A61K 9/16* (2013.01); *A61K 31/553* (2013.01); *A61P 35/00* (2018.01)

(58) Field of Classification Search
CPC ...... A61K 31/517; A61K 31/553; A61P 35/00
USPC ...................................................... 514/266
See application file for complete search history.

(56) References Cited

U.S. PATENT DOCUMENTS

| | | |
|---|---|---|
| 9,650,393 B2 | 5/2017 | Braun et al. |
| 10,851,091 B2 | 12/2020 | Braun et al. |
| 11,236,068 B2 | 2/2022 | Malhotra et al. |
| 2021/0252013 A1 | 8/2021 | Greene et al. |
| 2022/0081413 A1 | 3/2022 | Lim et al. |
| 2022/0152029 A1 | 5/2022 | Evangelista et al. |
| 2022/0152030 A1 | 5/2022 | Evangelista et al. |
| 2022/0193077 A1 | 6/2022 | Evangelista et al. |
| 2023/0089126 A1 | 3/2023 | Malhotra et al. |
| 2023/0250074 A1 | 8/2023 | Lebl et al. |
| 2023/0265074 A1 | 8/2023 | DiPasquale et al. |

FOREIGN PATENT DOCUMENTS

| | | | | |
|---|---|---|---|---|
| WO | WO-2020023297 A1 | * | 1/2020 | ........... A61K 31/155 |
| WO | WO-2020097537 A2 | * | 5/2020 | ........... A61K 31/517 |
| WO | 2022/035790 A1 | | 2/2022 | |
| WO | 2022/103904 A1 | | 5/2022 | |
| WO | 2022/103905 A1 | | 5/2022 | |
| WO | 2022/125427 A1 | | 6/2022 | |

OTHER PUBLICATIONS

Hong et al., KRASG12C Inhibition with Sotorasib in Advanced Solid Tumors, The New England Journal of Medicine, 2020, vol. 383 (13), pp. 1207-1217 (Year: 2020).*
Hong et al., "Abstract PD4-14: GDC-0077 is a selective PI3Kalpha inhibitor that demonstrates robust efficacy in PIK3CA mutant breast cancer models as a single agent and in combination with standard of care therapies" Cancer Res 78(4 Supplement):4-14 (2018).
Misale et al., "KRAS G12C NSCLC Models are Sensitive to Direct Targeting of KRAS in Combination with PI3K Inhibition" Clinical Cancer Research 25(2):796-807 (Jan. 15, 2019).
Palma et al., "Selective KRAS G12C inhibitors in non-small cell lung cancer: chemistry, concurrent pathway alterations, and clinical outcomes" NPJ precision oncology 5(98):1-9 (2021).
"International Search Report—PCT/US2023/017455" (w/Written Opinion),:pp. 1-12 (Sep. 20, 2023).
US Clinical Trials.gov, "A Study to Evaluate the Safety, Pharmacokinetics, and Activity of GDC-6036 Alone or in Combination in Participants With Advanced or Metastatic Solid Tumors With a KRAS G12C Mutation" (ClinicalTrials.gov ID: NCT04449874; Reference Study ID No. GO42144; History of Changes, v11, Submitted Date: Mar. 7, 2022; First Posted: Jun. 24, 2020; Last Update Posted: Jun. 23, 2023; Retrieved: Jul. 5, 2023),:1-17 (Jun. 23, 2023).

* cited by examiner

*Primary Examiner* — Jeffrey H Murray
*Assistant Examiner* — Rilla Marie Samsell
(74) *Attorney, Agent, or Firm* — Kevin M. Clark

(57) ABSTRACT

Provided herein are combination therapies comprising GDC-6036 and inavolisib and methods of using the same to treat cancer.

18 Claims, 10 Drawing Sheets

TREATMENT OF CANCER USING COMBINATION THERAPIES COMPRISING GDC-6036 AND GDC-0077

CROSS REFERENCE TO RELATED APPLICATIONS

This application claims the benefit of U.S. Provisional Patent Application No. 63/328,149, filed 6 Apr. 2022, which is incorporated herein in its entirety and for all purposes.

FIELD OF INVENTION

Provided herein are combination therapies comprising a $KRas^{G12C}$ inhibitor (e.g. GDC-6036) and a PI3K inhibitor (GDC-0077, inavolisib) and methods of using such combination therapies.

BACKGROUND

The Kirsten rat sarcoma viral oncogene homolog (KRAS) is a central component of the RAS/MAPK signal transduction pathway, an intracellular network of proteins that transmit extracellular growth factor signals to regulate cell proliferation, differentiation, and survival. Mutations in KRAS can result in alterations at several amino acids, including glycine 12 (G12), glycine 13, and glutamine 61, commonly found in solid tumors and associated with tumorigenesis and aggressive tumor growth. Oncogenic KRAS mutations that result in the change from G12 to cysteine (G12C) are prevalent in non-small cell lung cancer (NSCLC) (~12%), colorectal cancer (CRC) (~4%), and other tumor types (≤4%).

Advanced stage tumors harboring the $KRas^{G12C}$ mutation (hereafter referred to as $KRas^{G12C}$-positive tumors), including for example, lung cancer (e.g. NSCLC), CRC, and pancreatic cancer are incurable and carry a poor prognosis. Patients with advanced stage $KRas^{G12C}$-positive cancers may derive limited benefit from select chemotherapies and targeted therapies, thus, restricting effective available treatment options.

Phosphatidylinositol 3-kinase (PI3K) is a lipid kinase that upon activation by growth factor receptors and integrins regulates cell proliferation, survival, and migration. PI3K catalyzes the phosphorylation of phosphatidylinositol-4,5-bisphosphate ($PIP_2$) to generate phosphatidylinositol-3,4,5-triphosphate ($PIP_3$), a second messenger involved in the phosphorylation of AKT and other components in the AKT/mTOR pathway. Up to 70% of breast cancers have some form of molecular aberration of the PI3K/AKT/mTOR pathway. Activating mutations in PIK3CA, encoding the p110α subunit of PI3K, are highly prevalent in breast cancer and solid tumor malignancies.

While inhibitors of PI3Kα have been approved or in clinical development for the treatment of patients with hormone receptor (HR)-positive, HER2-negative, locally advanced or metastatic breast cancer with a PIK3CA mutation, there remains a need for effective therapies and combination therapies for treating cancers such as lung cancer, colorectal cancer, and pancreatic cancer harboring $KRas^{G12C}$ mutations.

SUMMARY

Provided herein are solutions to these and other problems in the art.

In one aspect provided herein is a combination therapy comprising GDC-6036 or a pharmaceutically acceptable salt thereof and inavolisib or a pharmaceutically acceptable salt thereof as described herein.

In another aspect provided herein is a method of treating lung cancer mediated by a $KRas^{G12C}$ mutation in a patient having such a lung cancer, the method comprising administering an effective amount of a combination therapy comprising administering an effective amount of GDC-6036 or a pharmaceutically acceptable salt thereof QD according to a dosing regimen comprising one or more cycles and an effective amount of inavolisib or a pharmaceutically acceptable salt thereof as described herein QD according to the dosing regimen comprising one or more cycles. In one such embodiment, the dosing regimen comprises 21 days or 28 days.

In another aspect provided herein is a method of treating lung cancer mediated by a $KRas^{G12C}$ mutation in a patient having such a cancer, the method comprising administering an effective amount of a combination therapy comprising GDC-6036 or a pharmaceutically acceptable salt thereof as described herein administered QD according to a dosing regimen comprising one or more 21-day cycles and an effective amount of inavolisib or a pharmaceutically acceptable salt thereof as described herein QD according to a dosing regimen comprising one or more 21-day cycles.

In another aspect provided herein is a method of treating a solid tumor mediated by a $KRas^{G12C}$ mutation in a patient having such a cancer, the method comprising administering an effective amount of a combination therapy comprising GDC-6036 or a pharmaceutically acceptable salt thereof as described herein administered QD according to a dosing regimen comprising one or more cycles as described herein and an effective amount of inavolisib or a pharmaceutically acceptable salt thereof as described herein QD according to a dosing regimen comprising one or more cycles as described herein.

In another aspect provided herein is a method of treating tissue agnostic cancer comprising a $KRas^{G12C}$ mutation in patient having such a cancer, the method comprising (i) determining the absence or presence of a KRasG12C mutation in a sample taken from a patient with a suspected diagnosed cancer; and (ii) where the patient sample comprises a KRasG12C mutation, administering an effective amount of a combination therapy comprising: (a) GDC-6036 or a pharmaceutically acceptable salt thereof administered QD according to a dosing regimen comprising one or more cycles as described herein; and (b) inavolisib or a pharmaceutically acceptable salt thereof administered QD according to a dosing regimen comprising one or more cycles as described herein.

In another aspect provided herein is the use of a combination therapy comprising GDC-6036 or a pharmaceutically acceptable salt thereof and inavolisib or a pharmaceutically acceptable salt thereof for the treatment of lung cancer, CRC, or pancreatic cancer as described herein.

In another aspect provided herein is the use of a combination therapy comprising GDC-6036 or a pharmaceutically acceptable salt thereof and inavolisib or a pharmaceutically acceptable salt thereof for the manufacture of a medicament for the treatment of lung cancer, CRC, or pancreatic cancer.

In embodiments of the methods and uses described herein, administration of inavolisib (GDC-0077) does not require pretesting or evaluation for the presence of one or more PI3KCA mutation.

BRIEF DESCRIPTION OF THE FIGURES

(FIG. 3A=H23 P; FIG. 3B=YSE410; FIG. 3C=H1792; FIG. 3D=H2122; FIG. 3E=HOP62; FIG. 3F=H2030; FIG. 3G=HCC4017; and FIG. 3H=HCC4019).

(FIG. 5A=SW1463; FIG. 5B=SW837; and FIG. 5C=HCC1263).

DETAILED DESCRIPTION

Definitions

Figure 1:
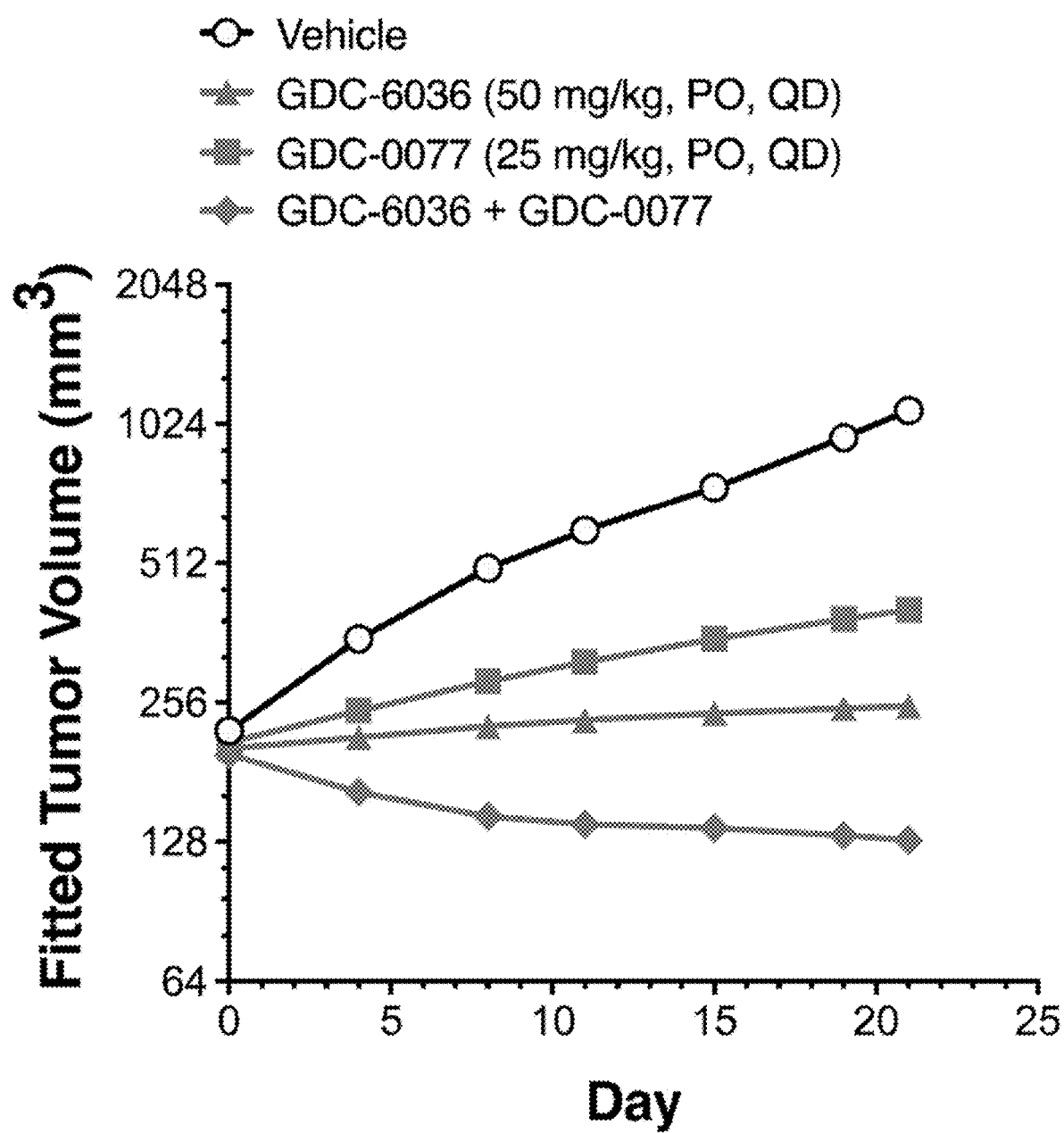
FIG. 1 depicts the fitted tumor volumes of treatment with GDC-6036 alone, GDC-0077 alone, or the combination of GDC-6036 and inavolisib. NCI-H2122 has lower sensitivity to KRAS-G12C inhibition; max effect is stasis. GDC-6036 alone: TGI=93%; GDC-0077 alone: TGI=74%; combination: TGI=113%.

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

A "KRas$^{G12C}$ inhibitor" as used herein refers to a covalent inhibitor that specifically binds to a mutant KRas protein comprising a Gly to Cys mutation at a position corresponding to residue 12.

"GDC-6036" refers to a compound having structure:

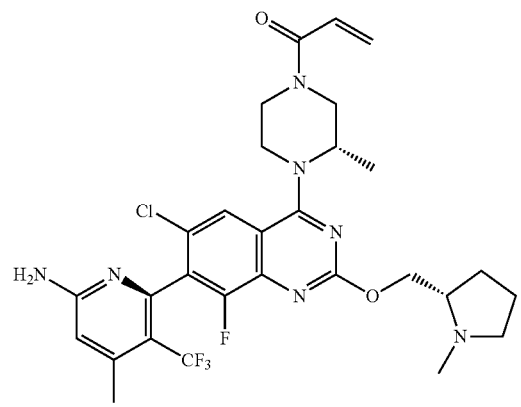

having the chemical name 1-((S)-4-((R)-7-(6-amino-4-methyl-3-(trifluoromethyl)pyridin-2-yl)-6-chloro-8-fluoro-2-MS)-1-methylpyrrolidin-2-yl)methoxy)quinazolin-4-yl)-3-methylpiperazin-1-yl)prop-2-en-1-one. In one embodiment, GDC-6036 is an adipate salt.

Inavolisib, CAS Registry Number 2060571-02-8, Genentech, Inc., U.S. Pat. No. 9,650,393; named as (S)-2-((2-((S)-4-(difluoromethyl)-2-oxooxazolidin-3-yl)-5,6-dihydrobenzo[f]imidazo[1,2-d][1,4]oxazepin-9-yl)amino) propanamide, refers to a compound having structure:

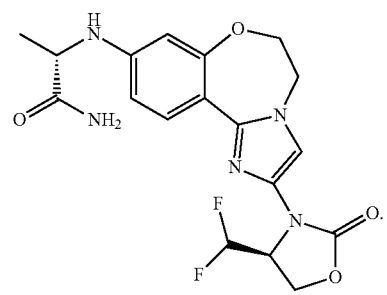 [SMILES: C[C@H](Nc1ccc2c(c1)OCCn1cc(N3C(=O)OC[C@H]3C(F)F)nc1-2)C(N)=O]

having the chemical name (2S)-2-[[2-[(4S)-4-(Difluoromethyl)-2-oxo-3-oxazolidinyl]-5,6-dihydroimidazo[1,2-d][1,4]benzoxazepin-9-yl]amino]propanamide. Inavolisib is also known as GDC-0077, RG6114, or RO7113755.

Inavolisib is a potent, orally bioavailable, clinical-stage, selective inhibitor of the Class I PI3K alpha isoform (PI3Kα), with >300-fold less potent biochemical inhibition for other Class I PI3K beta, delta, and gamma isoforms and increased potency in tumor cells bearing mutant PI3K over wild type (WT) PI3K cells (Braun, M. et al "Discovery of GDC-0077: A highly selective inhibitor of PI3K-alpha that induces degradation of mutant-p110 alpha protein" *Abstracts of Papers*, 254th ACS National Meeting & Exposition, Washington, DC, USA, Aug. 20-24, 2017, MEDI-22; Garland, K. et al "Discovery of novel class of alpha selective PI3K inhibitors" *Abstracts of Papers*, 254th ACS National Meeting & Exposition, Washington, DC, USA, Aug. 20-24, 2017, MEDI-103; Hong, R. et al "GDC-0077 is a selective PI3K alpha inhibitor that demonstrates robust efficacy in PIK3CA mutant breast cancer models as a single agent and in combination with standard of care therapies" 2017 *San Antonio Breast Cancer Symposium*, Dec. 5-9 2017, San Antonio, TX, Abstract Publication Number: PD4-14; Edgar, K. et al "Preclinical characterization of GDC-0077, a specific PI3K alpha inhibitor in early clinical development" *Cancer Research* 77(13 Supplement): Abstract 156·July 2017).

GDC-0077 exerts its activity by binding to the ATP binding site of PI3K, thereby inhibiting the phosphorylation of membrane-bound 4,5-phosphatidylinositol bisphosphate ($PIP_2$) to 3,4,5-phosphatidylinositol triphosphate ($PIP_3$). Inhibiting the phosphorylation of $PIP_2$ to $PIP_3$ decreases downstream activation of AKT and pS6, resulting in decreased cellular proliferation, metabolism, and angiogenesis. Nonclinical studies demonstrate that GDC-0077 specifically degrades mutant p110 alpha, inhibits proliferation and induces apoptosis of PIK3CA-mutant breast cancer cell lines, inhibits tumor growth in human breast xenograft models harboring PIK3CA mutations, and reduces downstream PI3K-pathway markers, including phosphorylated form of protein kinase B (pAKT), PRAS40 phosphorylated at Threonine 246 (pPRAS40), and S6RP phosphorylated at Serine 235/236 (pS6RP).

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids, which may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like. In one embodiment, the salt is formed with adipic acid.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The term "cancer" refers to a disease caused by an uncontrolled division of abnormal cells in a part of the body. In one embodiment, the cancer is lung cancer. In another embodiment, the cancer is non-small cell lung cancer (NSCLC). In another embodiment, the cancer is solid tumor. In another embodiment, the cancer is colorectal cancer (e.g. metastatic CRC), breast cancer, or pancreatic cancer. "Cancer" as used herein, refers to cancer characterized as having a $KRas^{G12C}$ mutation.

As used herein, "treating" comprises treatment with an effective amount of a therapeutic agent (e.g., GDC-6036 or inavolisib) or combination of therapeutic agents (e.g., GDC-6036 or inavolisib). In one embodiment, treating refers to treatment with an effective amount of GDC-6036 or a pharmaceutically acceptable salt thereof and inavolisib. The treatment may be first-line treatment (e.g., the patient may be previously untreated or not have received prior systemic therapy), or second line or later treatment. For example, a patient is successfully "treated" if one or more symptoms associated with a cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a cancer described herein. This delay can be of varying lengths of time, depending on the history of the cancer described herein and/or patient being treated. As is evident to one skilled in the art, a sufficient or significant delay can, in effect, encompass prevention, in that the patient does not develop the cancer.

Herein, an "effective amount" refers to the amount of a therapeutic agent described herein (e.g., GDC-6036 and/or inavolisib) that achieves a therapeutic result. In some examples, the effective amount of a therapeutic agent or a combination of therapeutic agents is the amount of the agent or of the combination of agents that achieves a clinical endpoint as provided herein. In one embodiment, an effective amount refers to the amount of GDC-6036 or a pharmaceutically acceptable salt thereof and the amount of inavolisib. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disease. An effective amount can be administered in one or more administrations. An effective amount of drug, compound, pharmaceutical composition, or combination therapy described herein can be an amount sufficient to accomplish therapeutic treatment either directly or indirectly.

"Objective response rate" or "ORR" refers the percentage of patients with a confirmed complete response or partial response on two consecutive occasions ≥4 weeks apart, as determined by the investigator according to RECIST v1.1.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

As used herein, "complete response" and "CR" refers to disappearance of all target lesions and (if applicable) normalization of tumor marker level.

As used herein, "partial response" and "PR" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

An "administration period" or "cycle" refers to a period of time comprising administration of one or more agents described herein (e.g. GDC-6036 and inavolisib) and an optional period of time comprising no administration of one or more of the agents described herein. For example, a cycle can be 21 days in total and include administration of one or more agents described herein (e.g. GDC-6036 and inavolisib) each day of the cycle. In another example, a cycle can be 28 days in total length and include administration of one or more agents described herein (e.g. GDC-6036 and inavolisib) for 21 days and a rest period of 7 days. A "rest period" refers to a period of time where at least one of the agents described herein (i.e. GDC-6036 and inavolisib) are not administered. In one embodiment, a rest period refers to a period of time where none of the agents described herein (i.e. GDC-6036 and inavolisib) are administered. A rest period as provided herein can in some instances include administration of another agent that is not GDC-6036 or inavolisib. In such instances, administration of another agent during a rest period should not interfere or detriment administration of an agent described herein. In one instance, cycle as used herein refers to 21 day cycles without a rest period. In another example, a cycle can be 28 days in total length and include administration of one or more agents described herein (e.g. GDC-6036 and inavolisib) QD for each day of the cycle.

A "dosing regimen" refers to an administration period of the agents described herein comprising one or more cycles, where each cycle can include administration of the agents described herein at different times or in different amounts.

"QD" refers to administration of an agent described herein once daily.

"BID" refers to administration of an agent described herein twice daily.

"PO" refers to oral administration of an agent described herein.

"IV" refers to intravenous administration of any agent described herein.

A graded adverse event refers to the severity grading scale as established for by NCI CTCAE. In one embodiment, the adverse event is graded in accordance with the table below.

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living [a] |
| 3 | Severe or medically significant, but not immediately life-threatening; hospitalization or prolongation of hospitalization indicated; disabling; or limiting self-care activities of daily living [b, c] |
| 4 | Life-threatening consequences or urgent intervention indicated [d] |
| 5 | Death related to adverse event [d] |

The term "patient" refers to a human patient. A patient may be an adult.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "in combination with" refers to administration of one treatment modality in addition to another treatment modality, for example, a treatment regimen that includes administration of inavolisib described herein and GDC-6036 or a pharmaceutically acceptable salt thereof. As such, "in combination with" refers to administration of one treatment modality before, during, or after administration of the other treatment modality to the patient.

A drug that is administered "concurrently" with one or more other drugs is administered during the same treatment cycle, on the same day of treatment, as the one or more other drugs, and, optionally, at the same time as the one or more other drugs. For instance, for cancer therapies given every 3 weeks, the concurrently administered drugs are each administered on day 1 of a 3 week cycle.

Combination Therapies

Provided herein are combination therapies (compositions) comprising a KRas$^{G12C}$ inhibitor (e.g. GDC-6036 or a pharmaceutically acceptable salt thereof (e.g. GDC-6036 adipate)) and a PI3K inhibitor (e.g. inavolisib) as described herein.

In one aspect provided herein is a combination therapy comprising GDC-6036 or a pharmaceutically acceptable salt thereof (e.g. GDC-6036 adipate) and inavolisib. In one embodiment, the combination therapies described herein are useful in the treatment of certain solid tumors comprising KRas$^{G12C}$ mutations.

In one embodiment, the combination therapies described herein are useful in the treatment of certain types of lung cancer as described herein comprising KRas$^{G12C}$ mutations. In one such embodiment, the lung cancer is non-small cell lung cancer (NSCLC) comprising a KRas$^{G12C}$ mutation.

In another embodiment, the combination therapies described herein are useful in the treatment of other solid tumors comprising a KRas$^{G12C}$ mutation. In one embodiment, the solid tumor is colorectal cancer, pancreatic cancer, or breast cancer.

In one aspect provided herein is a combination therapy comprising GDC-6036 or a pharmaceutically acceptable salt thereof administered QD according to a dosing regimen comprising one or more cycles and inavolisib administered QD according to a dosing regimen comprising one or more cycles. In such embodiments, evaluation for the presence of a KRasG12C mutation is performed and the combination therapy described herein is administered only when a KRasG12C mutation is present. In one such embodiment, no evaluation for the presence of mutant PIK3CA is performed.

In one embodiment, GDC-6036 or a pharmaceutically acceptable salt thereof is administered QD according to a dosing regimen comprising one or more 21-day cycles and inavolisib or a pharmaceutically acceptable salt thereof is administered QD according to a dosing regimen comprising one or more 21-day cycles. In one such embodiment, where the dosing regimen comprises one or more 21-day cycles, the dosing regimen comprises a rest period wherein one or both of GDC-6036 and inavolisib is not administered. In such embodiments, the combination therapies are useful in the treatment of a solid tumor comprising KRas$^{G12C}$ mutations as described herein (e.g. lung cancer). In one such embodiment, no evaluation for the presence of mutant PIK3CA is performed.

In another embodiment, GDC-6036 or a pharmaceutically acceptable salt thereof is administered QD according to a dosing regimen comprising one or more 28-day cycles and inavolisib or a pharmaceutically acceptable salt thereof is administered QD according to a dosing regimen comprising one or more 28-day cycles. In such embodiments, the combination therapies are useful in the treatment of a solid tumor comprising KRas$^{G12C}$ mutations as described herein (e.g. lung cancer). In one such embodiment, no evaluation for the presence of mutant PIK3CA is performed.

In one embodiment of the combination therapies described herein, GDC-6036 or a pharmaceutically acceptable salt thereof is administered as a fixed dose QD administration. In one embodiment, the administration is oral (PO), where GDC-6036 or a pharmaceutically acceptable salt thereof is formulated as a tablet or capsule. In one such embodiment, GDC-6036 or a pharmaceutically acceptable salt thereof is formulated (and administered) as a film coated tablet.

In one embodiment of the combination therapies described herein, GDC-6036 or a pharmaceutically acceptable salt thereof is administered at an amount of about 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-800 mg, 50 mg-700 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, GDC-6036 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, GDC-6036 or a pharmaceutically acceptable salt thereof is administered at an amount of about 100 mg, 200 mg, 300 mg, 400 mg, 500 mg, 600 mg, 700 mg, or 800 mg. In one such embodiment, GDC-6036 or a pharmaceutically acceptable salt thereof is administered at an amount of about 100 mg, 200 mg, or 400 mg. In one such embodiment, GDC-6036 or a pharmaceutically acceptable salt thereof is administered at an amount of about 100-300 mg. In one such embodiment, GDC-6036 or a pharmaceutically acceptable salt thereof is administered at an amount of about 200 mg. In one such embodiment, GDC-6036 or a pharmaceutically acceptable salt thereof is administered at an amount of about 300-600 mg. In another such embodiment, GDC-6036 or a pharmaceutically acceptable salt thereof is administered at an amount of about 400 mg. In one preferred embodiment, GDC-6036 of the combination therapies described herein is administered as an adipate salt. In such embodiments, the amount of GDC-6036 or a pharmaceutically acceptable salt thereof is administered as an amount relative to the free-base form.

The inclusion of one or therapeutic agents in a combination therapy can alter the efficacy and dosing amount of each agent in a dosing regimen. Thus, in one embodiment, the amount of GDC-6036 or a pharmaceutically acceptable salt thereof is administered as described herein at a lower starting dose for a whole or partial cycle described herein. In one embodiment, GDC-6036 may be administered at a lower dose for at least 1, 2, or 3 days prior to increasing the dose. In one such embodiment, the amount of GDC-6036 or a pharmaceutically acceptable salt thereof is a 200 mg starting dose. In another such embodiment, the amount of GDC-6036 or a pharmaceutically acceptable salt thereof is a a 300 mg starting dose. In such embodiments, the amount of GDC-6036 can be increased by 50 or 100 mg amounts (e.g. 200 mg starting dose to 250 or 300 mg dose: 300 mg dose to 400 mg dose). In one embodiment, the starting dose of GDC-6036 is 200 mg and the dose is increased to 400 mg.

In some embodiments, inavolisib is administered at an amount of 3, 6 or 9 mg, e.g., in one or more oral tablets. In some embodiments, inavolisib is adminstered orally at a 9 mg daily dose. In some of these embodiments, inavolisib is administered at an amount of 9 mg, e.g., in an oral tablet. In some embodiments, inavolisib is adminstered orally at a 6 mg daily dose, e.g., in one or more oral tablets. In some of these embodiments, inavolisib is administered at an amount of 3 mg, e.g., in an oral tablet.

In one embodiment, inavolisib is administered as a component of a combination therapy described herein at an amount of 6 mg QD in a dosing regimen comprising administration of each agent QD in a 21-day cycle. In another embodiment, inavolisib is administered as a component of a combination therapy described herein at an amount of 9 mg QD in a dosing regimen comprising administration of each agent QD in a 21-day cycle. In another embodiment, inavolisib is administered as a component of a combination therapy described herein at an amount of 3 mg QD in a dosing regimen comprising administration of each agent QD in a 21-day cycle. In one such embodiment, the amount of inavolisib administered is reduced from a starting dose to 6 mg or to 3 mg as described herein.

In one embodiment, the amount of inavolisib is lower as starting dose. In one such embodiment, the amount of inavolisib is 6 mg. In one such embodiment, the amount of inavolisib can be increased to 9 mg.

In one embodiment, the starting dose of GDC-6036 is 200 mg and the starting dose of inavolisib is 6 mg. In another embodiment, the starting dose of GDC-6036 is 400 mg and the starting dose of inavolisib is 6 mg. In still another embodiment, the starting dose of GDC-6036 is 200 mg and the starting dose of inavolisib is 9 mg.

In one embodiment, the combination therapies described herein are used for treating lung cancer comprising a KRas$^{G12C}$ mutation. In one such embodiment, the combination therapy comprises GDC-6036 or a pharmaceutically acceptable salt thereof (e.g. GDC-6036 adipate) and inavolisib where both agents are administered according to a dosing regimen comprising administration of each agent QD in a 21-day cycle. In another such embodiment, the combination therapy comprises GDC-6036 or a pharmaceutically acceptable salt thereof (e.g. GDC-6036 adipate) and inavolisib where both agents are administered according to a dosing regimen comprising administration of each agent QD in a 28-day cycle. In such embodiments, the lung cancer is non-small cell lung carcinoma (NSCLC). In one such embodiment, the lung cancer is adenocarcinoma, squamous-cell lung carcinoma or large-cell lung carcinoma. The lung cancer can be stage I or II lung cancer. In one embodiment, the lung cancer is stage III or IV lung cancer.

In another embodiment are combination therapies useful in the treatment of lung cancer comprising a KRas$^{G12C}$ mutation where the combination therapy comprises GDC-6036 or a pharmaceutically acceptable salt thereof (e.g. GDC-6036 adipate) where GDC-6036 is administered QD according to a dosing regimen comprising one or more 21-day cycles and inavolisib, where inavolisib is administered QD according to the dosing regimen comprising one or more 21-day cycles. In another embodiment, are combination therapies useful in the treatment of lung cancer comprising a KRas$^{G12C}$ mutation where the combination therapy comprises GDC-6036 or a pharmaceutically acceptable salt thereof (e.g. GDC-6036 adipate) where GDC-6036 is administered QD according to a dosing regimen comprising one or more 28-day cycles and inavolisib, where inavolisib is administered QD according to the dosing regimen comprising one or more 28-day cycles. In one preferred embodiment, the lung cancer is NSCLC (e.g. metastatic NSCLC).

In still another embodiment is a combination therapy useful in the treatment of lung cancer comprising a KRas$^{G12C}$ mutation where the combination therapy comprises GDC-6036 or a pharmaceutically acceptable salt thereof (e.g. GDC-6036 adipate) where GDC-6036 is administered QD at an amount of about 50 mg-500 mg according to the dosing regimen comprising one or more 21-day cycles and inavolisib, where inavolisib is administered QD at an amount of about 3 mg, 6 mg, or 9 mg according to the dosing regimen comprising one or more 21-day cycles. In one such embodiment, inavolisib is administered at an amount of 6 mg. In another embodiment, inavolisib is administered at an amount of 9 mg. In another embodiment, inavolisib is administered at an amount of 3 mg. In one embodiment, the lung cancer is NSCLC. In one embodiment, GDC-6036 is administered at 200 or 400 mg and inavolisib is administered at 6 or 9 mg.

In still another embodiment is a combination therapy useful in the treatment of lung cancer comprising a KRas$^{G12C}$ mutation where the combination therapy comprises GDC-6036 or a pharmaceutically acceptable salt thereof (e.g. GDC-6036 adipate) where GDC-6036 is administered QD at an amount of about 50 mg-500 mg according to the dosing regimen comprising one or more 28-day cycles and inavolisib, where inavolisib is administered QD at an amount of about 3 mg, 6 mg, or 9 mg according to the dosing regimen comprising one or more 28-day cycles. In one such embodiment, inavolisib is administered at an amount of 6 mg. In another embodiment, inavolisib is administered at an amount of 9 mg. In another embodiment, inavolisib is administered at an amount of 3 mg. In one embodiment, the lung cancer is NSCLC. In one embodiment, GDC-6036 is administered at 200 or 400 mg and inavolisib is administered at 6 or 9 mg.

In still another embodiment are combination therapies described herein that are useful in the treatment of solid tumors comprising a KRas$^{G12C}$ mutation. In one particular embodiment, the combination therapy comprises GDC-6036 or a pharmaceutically acceptable salt thereof (e.g. GDC-6036 adipate) and inavolisib, where the combination therapy is for treating a solid tumor comprising a KRas$^{G12C}$ mutation as described herein. In one such embodiment, the solid tumor is CRC, breast cancer, or pancreatic cancer. In one embodiment, GDC-6036 is administered at 200 or 400 mg and inavolisib is administered at 6 or 9 mg.

In another embodiment are combination therapies useful in the treatment of a solid tumor described herein comprising a KRas$^{G12C}$ mutation where the combination therapy comprises GDC-6036 or a pharmaceutically acceptable salt thereof (e.g. GDC-6036 adipate) where GDC-6036 is administered QD at an amount as described herein according to a dosing regimen comprising one or more 21-day cycles and inavolisib, where inavolisib is administered QD according to the dosing regimen comprising one or more 21-day cycles in an amount of about 3 mg, 6 mg, or 9 mg. In one embodiment, GDC-6036 is administered at 200 or 400 mg and inavolisib is administered at 6 or 9 mg.

In another embodiment are combination therapies useful in the treatment of a solid tumor described herein comprising a KRas$^{G12C}$ mutation where the combination therapy comprises GDC-6036 or a pharmaceutically acceptable salt thereof (e.g. GDC-6036 adipate) where GDC-6036 is administered QD at an amount as described herein according to a dosing regimen comprising one or more 28-day cycles and inavolisib, where inavolisib is administered QD according to the dosing regimen comprising one or more 28-day cycles in an amount of about 3 mg, 6 mg, or 9 mg. In one embodiment, GDC-6036 is administered at 200 or 400 mg and inavolisib is administered at 6 or 9 mg.

In still another embodiment are combination therapies described herein that are useful in the treatment of tissue agnostic cancer comprising a KRas$^{G12C}$ mutation. In one particular embodiment, the combination therapy comprises GDC-6036 or a pharmaceutically acceptable salt thereof (e.g. GDC-6036 adipate) and inavolisib, where the combination therapy is for treating a tissue agnostic cancer comprising a KRas$^{G12C}$ mutation as described herein.

In another embodiment are combination therapies useful in the treatment of a tissue agnostic cancer comprising a KRas$^{G12C}$ mutation where the combination therapy comprises GDC-6036 or a pharmaceutically acceptable salt thereof (e.g. GDC-6036 adipate) where GDC-6036 is administered QD at an amount as described herein according to a dosing regimen comprising one or more 21-day cycles and inavolisib, where inavolisib is administered QD according to the dosing regimen comprising one or more 21-day cycles in an amount of about 3 mg, 6 mg, or 9 mg. In one embodiment, GDC-6036 is administered at 200 or 400 mg and inavolisib is administered at 6 or 9 mg.

In another embodiment are combination therapies useful in the treatment of a tissue agnostic cancer comprising a KRas$^{G12C}$ mutation where the combination therapy comprises GDC-6036 or a pharmaceutically acceptable salt thereof (e.g. GDC-6036 adipate) where GDC-6036 is administered QD at an amount as described herein according to a dosing regimen comprising one or more 28-day cycles and inavolisib, where inavolisib is administered QD according to the dosing regimen comprising one or more 28-day cycles in an amount of about 3 mg, 6 mg, or 9 mg. In one embodiment, GDC-6036 is administered at 200 or 400 mg and inavolisib is administered at 6 or 9 mg.

Methods of Treatments

In one aspect provided herein is a method of treating lung cancer comprising a KRas$^{G12C}$ mutation in a patient having such a lung cancer, the method comprising administering to the patient an effective amount of a combination therapy comprising GDC-6036 or a pharmaceutically acceptable salt thereof (e.g. GDC-6036 adipate) and inavolisib.

In one embodiment of the methods provided herein, the lung cancer is non-small cell lung carcinoma (NSCLC). In another embodiment of the methods provided herein, the lung cancer is adenocarcinoma, squamous-cell lung carcinoma or large-cell lung carcinoma. In one such embodiment, the cancer is lung adenocarcinoma. In another such embodiment, the lung cancer is a small cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer.

Also provided herein is a method (M1) of treating NSCLC comprising a KRas$^{G12C}$ mutation in a patient having such a cancer, where the method comprises administering to the patient an effective amount of a combination therapy as described herein comprising (i) GDC-6036 or a pharmaceutically acceptable salt thereof QD according to a dosing regimen comprising one or more 21-day cycles; and (ii) inavolisib QD according to the dosing regimen comprising one or more 21-day cycles. In one embodiment of the method provided herein, the method is for treating adenocarcinoma. In one embodiment of the method provided herein, the method comprises 2 or more cycles. In one such embodiment, the method is for treating first-line NSCLC.

Also provided herein is a method (M2) of treating NSCLC comprising a KRas$^{G12C}$ mutation in a patient having such a cancer, where the method comprises administering to the patient an effective amount of a combination therapy as described herein comprising (i) GDC-6036 or a pharmaceutically acceptable salt thereof QD according to a dosing regimen comprising one or more 28-day cycles; and (ii) inavolisib QD according to the dosing regimen comprising one or more 28-day cycles. In one embodiment of the method provided herein, the method is for treating adenocarcinoma. In one embodiment of the method provided herein, the method comprises 2 or more cycles. In one such embodiment, the method is for treating first-line NSCLC.

Also provided herein is a method (M3) of treating NSCLC comprising a KRas$^{G12C}$ mutation in a patient having such a cancer, where the method comprises administering to the patient an effective amount of a combination therapy as described herein comprising a dosing regimen comprising: (i) administering 50 mg-500 mg of GDC-6036 or a pharmaceutically acceptable salt thereof QD according to a dosing regimen comprising one or more 21-day cycles; and (ii) administering about 3 mg, 6 mg, or 9 mg of inavolisib QD according to the dosing regimen comprising one or more 21-day cycles. In one such embodiment, the dosing regimen includes a rest period where one or both of GDC-6036 and/or inavolisib is not administered. In one embodiment, GDC-6036 is administered at 200 or 400 mg and inavolisib is administered at 6 or 9 mg.

Also provided herein is a method (M4) of treating NSCLC comprising a KRas$^{G12C}$ mutation in a patient having such a cancer, where the method comprises administering to the patient an effective amount of a combination therapy as described herein comprising a dosing regimen comprising: (i) administering 50 mg-500 mg of GDC-6036 or a pharmaceutically acceptable salt thereof QD according to a dosing regimen comprising one or more 28-day cycles; and (ii) administering about 3 mg, 6 mg, or 9 mg of inavolisib QD according to the dosing regimen comprising one or more 28-day cycles. In one embodiment, GDC-6036 is administered at 200 or 400 mg and inavolisib is administered at 6 or 9 mg.

In embodiments M1-M4, the methods can further comprise (a) determining the absence or presence of a KRasG12C mutation in a sample taken from a patient with a suspected diagnosed cancer; and (b) administering to the patient a combination therapy as described herein comprising an effective amount of GDC-6036 or a pharmaceutically acceptable salt thereof and inavolisib as described herein. In one such embodiment, the method further comprises (c) no evaluation for the presence of mutant PIK3CA before administration of inavolisib as described herein.

In another aspect provided herein is a method (M5) for treating a solid tumor comprising a KRas$^{G12C}$ mutation in a patient having such a solid tumor, the method comprising administering to the patient an effective amount of a combination therapy comprising GDC-6036 or a pharmaceutically acceptable salt thereof (e.g. GDC-6036 adipate) and inavolisib. In one such embodiment, the method comprises administering to the patient an effective amount of a combination therapy as described herein comprising: (i) GDC-6036 or a pharmaceutically acceptable salt thereof administered QD according to a dosing regimen comprising one or more 21-day cycles; and (ii) inavolisib or a pharmaceutically acceptable salt thereof administered QD according to the dosing regimen comprising one or more 21-day cycles. In one such embodiment, the dosing regimen includes a rest period where one or both of GDC-6036 and/or inavolisib are not administered. In one such embodiment, the rest period is 7 days.

In another aspect provided herein is a method (M6) for treating a solid tumor comprising a KRas$^{G12C}$ mutation in a patient having such a solid tumor, the method comprising administering to the patient an effective amount of a combination therapy as described herein comprising: (i) GDC-6036 or a pharmaceutically acceptable salt thereof administered QD according to a dosing regimen comprising one or more 28-day cycles; and (ii) inavolisib or a pharmaceutically acceptable salt thereof administered QD according to the dosing regimen comprising one or more 28-day cycles. In one embodiment of the method M5 or M6 provided herein, the method comprises 2 or more cycles. In one such embodiment of the method M5 or M6, GDC-6036 is administered at an amount of about 50 mg-500 mg and inavolisib is administered at an amount of 3 mg, 6 mg, or 9 mg. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed, prior to administration of a combination therapy described herein. In one embodiment of the method M5 or M6 described herein, the solid tumor is colorectal cancer (CRC). In one such embodiment, the CRC is metastatic CRC (mCRC).

Further provided herein is a method (M7) of treating tissue agnostic cancer comprising a KRasG12C mutation in patient having such a cancer, where the method comprises (i) determining the absence or presence of a KRasG12C mutation in a sample taken from a patient with a suspected diagnosed cancer; and (ii) where the patient sample comprises a KRasG12C mutation, administering an effective amount of a combination therapy comprising (a) GDC-6036 or a pharmaceutically acceptable salt thereof administered QD according to a dosing regimen comprising one or more 21-day cycles; and (b) inavolisib or a pharmaceutically acceptable salt thereof administered QD according to the dosing regimen comprising one or more 21-day cycles. In one such embodiment, the patient sample is not evaluated for the presence of mutant PIK3CA prior to administration of inavolisib as described herein. In one such embodiment of the method M7, the dosing regimen includes a rest period where one or both of GDC-6036 and/or inavolisib are not administered. In one such embodiment, the rest period is 7 days.

Further provided herein is a method (M8) of treating tissue agnostic cancer comprising a KRasG12C mutation in patient having such a cancer, where the method comprises (i) determining the absence or presence of a KRasG12C mutation in a sample taken from a patient with a suspected diagnosed cancer; and (ii) where the patient sample comprises a KRasG12C mutation, administering an effective amount of a combination therapy comprising (a) GDC-6036 or a pharmaceutically acceptable salt thereof administered QD according to a dosing regimen comprising one or more 28-day cycles; and (b) inavolisib or a pharmaceutically acceptable salt thereof administered QD according to the dosing regimen comprising one or more 28-day cycles. In one such embodiment, the patient sample is not evaluated for the presence of mutant PIK3CA prior to administration of inavolisib as described herein.

In one embodiment of the methods M7 and M8, the patient sample is further analyzed for the absence or presence of PI3K mutations such as those described herein.

In one embodiment of the methods described herein, GDC-6036 or a pharmaceutically acceptable salt thereof is administered at an amount of about 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-800 mg, 50 mg-700 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, GDC-6036 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, GDC-6036 or a pharmaceutically acceptable salt thereof is administered at an amount of about 100 mg, 200 mg, 300 mg, 400 mg, 500 mg, 600 mg, 700 mg, or 800 mg. In another embodiment, GDC-6036 or a pharmaceutically acceptable salt thereof is administered at an amount of about 100 mg, 200 mg, or 400 mg. In one embodiment, GDC-6036 or a pharmaceutically acceptable salt thereof is administered QD as described herein at an amount of 100 mg. In one embodiment, GDC-6036 or a pharmaceutically acceptable salt thereof is administered QD as described herein at an amount of 200 mg. In one embodiment, GDC-6036 or a pharmaceutically acceptable salt thereof is administered QD as described herein at an amount of 400 mg. In another embodiment, GDC-6036 or a pharmaceutically acceptable salt thereof is administered at an amount of about 100-300 mg. In another such embodiment, GDC-6036 or a pharmaceutically acceptable salt thereof is administered at an amount of about 300-600 mg. In one preferred embodiment, GDC-6036 of the combination therapies described herein is administered as an adipate salt. In such embodiments, the amount of GDC-6036 or a pharmaceutically acceptable salt thereof is administered as an amount relative to the free-base form.

In one embodiment, inavolisib is administered QD as described herein at an amount of 6 mg. In another embodiment, inavolisib is administered QD as described herein at an amount of 9 mg. In another embodiment, inavolisib is administered QD as described herein at an amount of 3 mg.

In one embodiment, GDC-6036 or a pharmaceutically acceptable salt thereof is administered according to the methods described herein at an amount of 200 mg and inavolisib is administered according to the methods described herein at an amount of 6 mg. In one embodiment, GDC-6036 or a pharmaceutically acceptable salt thereof is administered according to the methods described herein at an amount of 400 mg and inavolisib is administered according to the methods described herein at an amount of 6 mg. In one embodiment, GDC-6036 or a pharmaceutically acceptable salt thereof is administered according to the methods described herein at an amount of 200 mg and inavolisib is administered according to the methods described herein at an amount of 3 mg. In one embodiment, GDC-6036 or a pharmaceutically acceptable salt thereof is administered according to the methods described herein at an amount of 200 mg and inavolisib is administered according to the methods described herein at an amount of 9 mg. In one embodiment, GDC-6036 or a pharmaceutically acceptable salt thereof is administered according to the methods described herein at an amount of 400 mg and inavolisib is administered according to the methods described herein at an amount of 3 mg. In one embodiment, GDC-6036 or a pharmaceutically acceptable salt thereof is administered according to the methods described herein at an amount of 400 mg and inavolisib is administered according to the methods described herein at an amount of 9 mg.

In certain instances, the amount of inavolisib adminstered may be adjusted from a starting administered amount of 6 mg to 9 mg. Where a patient described herein is administered 6 mg of inavolisib as described herein, and such administration is not tolerated, the amount of inavolisib administered to the patient can be decreased to 3 mg. Likewise, where a patient described herein is administered 9 mg of inavolisib as described herein, and such administration is not tolerated, the amount of inavolisib administered to the patient can be decreased to 6 mg or to 3 mg. As used herein "tumor agnostic" refers to any solid tumor tested for the presence of a $KRas^{G12C}$ mutation as described herein.

The methods provided herein can include administration of a combination therapy described herein as part of a dosing regimen. In such one embodiment, the dosing regimen comprises one or more cycles. In another embodiment, the dosing regimen comprises at least 2 cycles. In another embodiment, the dosing regimen comprises 2-3 cycles. In still another embodiment, the dosing regimen comprises at least 4, 6, 8, 10, or 12 cycles. In another aspect provided herein is the dosing regimen comprises 2, 3, 4, 5, 6, 8, 10, 12, 16, 18, 20, 24, 30, 36, 42, 48, 54, 60, 66, or 72 cycles. In still another embodiment, dosing regimen comprises about 2-72, 2-66, 2-60, 2-54, 2-48, 2-42, 2-36, 2-30, 2-24, 2-18, 2-12, or 2-6 cycles. In one embodiment, the dosing regimen includes administration of a combination therapy as described herein in any number of cycles until the desired response (e.g. PFS, OS, ORR, and/or DOR) reaches a desired outcome (e.g. increase in PFS, OS, ORR, and/or DOR compared to a control described herein). In another embodiment, the dosing regimen includes administration of a combination therapy as described herein in any number of cycles until toxicity develops or the patient otherwise experiences one or more adverse events (AEs) that prevents further administration. In such embodiments, the amount of an agent administered (e.g. GDC-6036 or a pharmaceutically acceptable salt thereof or inavolisib) can be adjusted to decrease or eliminate the AE and permit addition cycles in the dosing regimen. In still another embodiment, the dosing regimen includes administration of a combination therapy as described herein in any number of cycles until disease progression.

In some instances, the methods described herein include administration of one or more additional therapies where the additional therapy is one or more side-effect limiting agents (e.g., agents intended to lessen the occurrence and/or severity of side effects of treatment, such as anti-nausea agents, a corticosteroid (e.g., prednisone or an equivalent, e.g., at a dose of 1-2 mg/kg/day), hormone replacement medicine(s), and the like).

A patient as provided herein must be evaluated and have a confirmed test result for a KRas$^{G12C}$ mutation as set forth herein. In one such embodiment, the patient has been previously treated with one or more prior therapies. A patient described herein having diagnosed NSCLC and a confirmed test result for a KRas$^{G12C}$ mutation must not have a known concomitant second oncogenic driver (e.g., for NSCLC: sensitizing EGFR mutations, ALK rearrangement, ROS1 rearrangement, BRAF V600E mutation, NTRK fusions, RET fusions; or for adenocarcinoma of the colon or rectum: BRAF V600E mutation, ERBB2 amplification). In one such embodiment, the patient has been previously treated with one or more prior therapies. In one embodiment, such second oncogenic drivers are determined using NGS (e.g. by the Foundation Medicine, Inc. (FMI) NGS assay).

In one embodiment, a patient as provided herein must be evaluated and have a confirmed test result for a KRas$^{G12C}$ mutation as set forth herein and the patient has not been evaluated for the presence of mutant PIK3CA having mutations at one or more of positions 88, 106, 111, 118, 345, 420, 453, 542, 545, 546, 1043, 1047 and 1049 (e.g. H1047, E545, E542, Q546, N345, C420, M1043, G1049, E453, K111, G106, G118, and R88).

In one embodiment, a patient described herein has received prior treatment with a KRas$^{G12C}$ specific inhibitor.

In another embodiment, a patient described herein has not received treatment with chemotherapy, immunotherapy, or biologic therapy as anti-cancer therapy within 3 weeks prior to administration of a combination therapy described herein, or endocrine therapy within 2 weeks prior to administration of a combination therapy described herein, except for the following:

(a) hormonal therapy with gonadotropin-releasing hormone (GnRH) agonists or antagonists for endocrine sensitive cancers (e.g., prostate, endometrial, hormone receptor-positive breast cancer);

(b) kinase inhibitors, approved by regulatory authorities, may be used up to 2 weeks prior to administration of a combination therapy described herein, provided any drug-related toxicity has completely resolved; or (c) treatment with an investigational agent within 3 weeks or five half-lives prior to administration of a combination therapy described herein, whichever is shorter.

In another embodiment, a patient described herein has not received radiation therapy (other than palliative radiation to bony metastases and radiation to CNS metastases as described above) as cancer therapy within 4 weeks prior to initiation of administration of a combination therapy described herein. In still another embodiment, a patient described herein has not received palliative radiation to bony metastases within 2 weeks prior to administration of a combination therapy described herein.

In another embodiment, a patient described herein does not have a history of idiopathic pulmonary fibrosis, organizing pneumonia (e.g., bronchiolitis obliterans), drug-induced pneumonitis, or idiopathic pneumonitis, or evidence of active pneumonitis on screening chest computed tomography (CT) scan.

Further provided herein is the use (UL1) of a combination therapy described herein comprising GDC-6036 or a pharmaceutically acceptable salt thereof and inavolisib for the treatment of lung cancer as described herein. In one embodiment, is a use (UL2) of a combination therapy described herein comprising GDC-6036 or a pharmaceutically acceptable salt thereof and inavolisib for the treatment of NSCLC as described herein.

Further provided herein is the use (UL3) of a combination therapy for the treatment of lung cancer as described herein wherein the combination therapy comprises: (i) GDC-6036 or a pharmaceutically acceptable salt thereof administered QD according to a dosing regimen comprising one or more 21-day cycles; and (ii) inavolisib administered QD on according to the dosing regimen comprising one or more 21-day cycles. In one such embodiment, GDC-6036 or a pharmaceutically acceptable salt thereof is administered at an amount of about 50-500 mg. In another such embodiment, inavolisib is administered at an amount of about 6 mg. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UL4) of a combination therapy for the treatment of lung cancer as described herein wherein the combination therapy comprises: (i) GDC-6036 or a pharmaceutically acceptable salt thereof administered QD according to a dosing regimen comprising one or more 28-day cycles; and (ii) inavolisib administered QD on according to the dosing regimen comprising one or more 28-day cycles. In one such embodiment, GDC-6036 or a pharmaceutically acceptable salt thereof is administered at an amount of about 50-500 mg. In another such embodiment, inavolisib is administered at an amount of about 6 mg. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UL5) of a combination therapy described herein for the treatment of lung cancer as described herein wherein the combination therapy comprises: (i) GDC-6036 or a pharmaceutically acceptable salt thereof administered at an amount of about 50-500 mg QD according to a dosing regimen comprising one or more 21-day cycles; and (ii) inavolisib administered at an amount of 3 mg, 6 mg, or 9 mg QD according to the dosing regimen comprising one or more 21-day cycle. In one such embodiment, the dosing regimen includes 2 or more cycles as described herein. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UL6) of a combination therapy described herein for the treatment of lung cancer as described herein wherein the combination therapy comprises: (i) GDC-6036 or a pharmaceutically acceptable salt thereof administered at an amount of about 50-500 mg QD according to a dosing regimen comprising one or more 28-day cycles; and (ii) inavolisib administered at an amount of 3 mg, 6 mg, or 9 mg QD according to the dosing regimen comprising one or more 28-day cycle. In one such embodiment, the dosing regimen includes 2 or more cycles as described herein. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UL7) of a combination therapy described herein comprising GDC-6036 or a pharmaceutically acceptable salt thereof and inavolisib for the manufacture of a medicament for the treatment of lung cancer as described herein.

Further provided herein is the use (UL8) of a combination therapy described herein for the manufacture of a medicament for the treatment of lung cancer as described herein wherein the combination therapy comprises: (i) GDC-6036 or a pharmaceutically acceptable salt thereof administered QD according to a dosing regimen comprising one or more 21-day cycles; and (ii) inavolisib administered QD according to the dosing regimen comprising one or more 21-day cycles. In one such embodiment, GDC-6036 or a pharmaceutically acceptable salt thereof is administered at an amount of about 50-500 mg. In another such embodiment, inavolisib is administered at an amount of about 3 mg, 6 mg, or 9 mg. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UL9) of a combination therapy described herein for the manufacture of a medicament for the treatment of lung cancer as described herein wherein the combination therapy comprises: (i) GDC-6036 or a pharmaceutically acceptable salt thereof administered QD according to a dosing regimen comprising one or more 28-day cycles; and (ii) inavolisib administered QD according to the dosing regimen comprising one or more 28-day cycles. In one such embodiment, GDC-6036 or a pharmaceutically acceptable salt thereof is administered at an amount of about 50-500 mg. In another such embodiment, inavolisib is administered at an amount of about 3 mg, 6 mg, or 9 mg. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

In such embodiments of the uses (UL1-UL8) described herein, a patient described herein is diagnosed with NSCLC mediated by a KRas$^{G12C}$ mutation.

Further provided herein is the use (UC1) of a combination therapy described herein comprising GDC-6036 or a pharmaceutically acceptable salt thereof and inavolisib for the treatment of solid tumors as described herein.

Further provided herein is the use (UC2) of a combination therapy described herein for the treatment of a solid tumor as described herein wherein the combination therapy comprises: (i) GDC-6036 or a pharmaceutically acceptable salt thereof administered QD at an amount of about 50-500 mg according to a dosing regimen comprising one or more 21-day cycles; and (ii) inavolisib administered QD at an amount of 3 mg, 6 mg, or 9 mg according to the dosing regimen comprising one or more 21-day cycles. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UC3) of a combination therapy described herein for the treatment of a solid tumor as described herein wherein the combination therapy comprises: (i) GDC-6036 or a pharmaceutically acceptable salt thereof administered QD at an amount of about 50-500 mg according to a dosing regimen comprising one or more 28-day cycles; and (ii) inavolisib administered QD at an amount of 3 mg, 6 mg, or 9 mg according to the dosing regimen comprising one or more 28-day cycles. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

In such embodiments of the uses UC1-UC3 described herein, a patient described herein is diagnosed with CRC mediated by a KRas$^{G12C}$ mutation.

Further provided herein is the use (UA1) of a combination therapy described herein for the treatment of tissue agnostic cancer comprising a KRasG12C mutation as described herein wherein a sample taken from a patient with a suspected diagnosed cancer is tested for the absence or presence of a KRasG12C mutation; and where the patient sample comprises a KRasG12C mutation, administering an effective amount of a combination therapy: (a) GDC-6036 or a pharmaceutically acceptable salt thereof administered QD at an amount of about 50-500 mg QD according to a dosing regimen comprising one or more 21-day cycles; and (b) inavolisib administered QD at an amount of 3 mg, 6 mg, or 9 mg according to the dosing regimen comprising one or more 21-day cycles. In such embodiments, GDC-6036 and inavolisib can be administered as described herein and in accordance with the uses and methods provided herein. In one embodiment, GDC-6036 is administered at 200 or 400 mg and inavolisib is administered at 6 or 9 mg. In another embodiment, the patient is evaluated for the presence of a KRasG12C mutation, but no evaluation for the presence of mutant PIK3CA is performed prior to administration of a combination therapy described herein.

Further provided herein is the use (UA2) of a combination therapy described herein for the treatment of tissue agnostic cancer comprising a KRasG12C mutation as described herein wherein a sample taken from a patient with a suspected diagnosed cancer is tested for the absence or presence of a KRasG12C mutation; and where the patient sample comprises a KRasG12C mutation, administering an effective amount of a combination therapy: (a) GDC-6036 or a pharmaceutically acceptable salt thereof administered QD at an amount of about 50-500 mg QD according to a dosing regimen comprising one or more 28-day cycles; and (b) inavolisib administered QD at an amount of 3 mg, 6 mg, or 9 mg according to the dosing regimen comprising one or more 28-day cycles. In such embodiments, GDC-6036 and inavolisib can be administered as described herein and in accordance with the uses and methods provided herein. In one embodiment, the patient sample is not evaluated for the presence of mutant PIK3CA prior to administration of a combination therapy described herein.

In one embodiment of the uses UA1 and UA2, the patient sample is further analyzed for the absence or presence of PI3K mutations such as those described herein.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. GDC-6036 or a pharmaceutically acceptable salt thereof and inavolisib) is administered in a dosing regimen comprising a staggered dosing schedule. In one such embodiment, the patient has a reduced number or grade of adverse events (AEs) comparable to a control (e.g. SOC therapy, treatment with one agent described herein (e.g. GDC-6036 or inavolisib alone).

It is generally understood that the when an adverse event occurs, four options exist: (1) continue treatment as-is with optional concomitant therapy; (2) adjust the dose of one or more agents in the dosing regimen; (3) suspend administration of one or more agents in the dosing regimen; or (4) discontinue administration of one or more agents in the dosing regimen. In one embodiment, the amount of GDC-6036 administered is not modified. In another embodiment, the amount of inavolisib administered is not modified. In one embodiment, where the administration of an agent described herein (e.g. GDC-6036 or a pharmaceutically acceptable salt thereof or inavolisib is interrupted, the next administration of the respective agent occurs on the same day as administration of GDC-6036 is resumed. In one embodiment, GDC-6036 or a pharmaceutically acceptable salt thereof is administered without food (i.e. a patient should not eat at least 2 hours before and 1 hour after administration).

In one embodiment, a patient described herein experiences gastrointestinal toxicity as an AE at a grade of less than or equal to 2. In one such embodiment, the gastrointestinal toxicity is diarrhea, nausea, or vomitting. In another embodiment, a patient described herein experiences phototoxicity. In such embodiments, the patient should wear sunscreen and protective clothing outdoors.

Patients described herein can also be administered concomitant therapies including: (a) anti-seizure medications or warfarin; (b) oral contraceptives or other allowed maintenance therapy; (c) anti-emetics and anti-diarrheal medications provided that such medications should not be administered prophylactically before initial treatment with study drug; (d) pain medications administered per standard clinical practice; (e) bisphosphonate and denosumab therapy for bone metastases or osteopenia/osteoporosis; or (f) multivitamins, calcium, and vitamins C, D, and E supplements.

Patients described herein may not concomitantly take therapies including (1) Strong/moderate CYP3A4 inhibitors (e.g. atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements) or (2) Strong/moderate CYP3A4 inducers (e.g. rifampin, carbamazepine, phenytoin, oxcarbazepine, phenobarbital, efavirenz, nevirapine, etravirine, modafinil, hyperforin (St. John's Wort), and cyproterone).

In another embodiment, a patient described herein is not administered a drug that reduces gastric acid production, such as proton pump inhibitors or H2-receptor antagonists.

In another embodiment, patients described herein are not administered any of the following therapies:
  (a) Any other investigational therapy (excluding GDC-6036 or inavolisib) within 3 weeks or five half-lives prior to administration of a combination therapy described herein, whichever is shorter, or during such treatment;
  (b) Concomitant therapy intended for the treatment of cancer whether approved by the FDA or experimental, including chemotherapy, radiotherapy, immunotherapy, biologic therapy, herbal therapy, or hormonal therapy except for the following:
    (i) Hormonal therapy with gonadotropin-releasing hormone (GnRH) agonists or antagonists for endocrine sensitive cancers (e.g., prostate, endometrial, hormone receptor-positive breast cancer);
    (ii) Hormone replacement therapy or oral contraception;
  (c) Radiotherapy for unequivocal progressive disease with the exception of new brain metastases in the setting of systemic response as follows: patients who have demonstrated control of their systemic disease (defined as having received clinical benefit [i.e., a PR, CR, or SD for ≥3 months]), but who have developed brain metastases that are treatable with radiation, will be allowed to continue to receive therapy with GDC-6036 during the study until they either experience systemic progression of their disease and/or further progression in the brain (based on investigator assessments).
  (d) Quinidine or other anti-arrhythmic agents; or
  (e) Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1;

In one embodiment of such methods, the patient is diagnosed with a cancer described herein. In another embodiment of such methods, the sample is a tumor sample taken from the subject. In one such embodiment, the sample is taken before administration of any therapy described herein. In another such embodiment, the sample is taken before administration of at least one agent described herein. In some embodiments, tumor samples can be taken at specified intervals during treatment with a combination therapy described herein to assess treatment.

Determining whether a tumor or cancer comprises a $KRas^{G12C}$ mutation can be undertaken by assessing the nucleotide sequence encoding the K-Ras protein, by assessing the amino acid sequence of the K-Ras protein, or by assessing the characteristics of a putative K-Ras mutant protein. The sequence of wild-type human K-Ras (e.g. Accession No. NP203524) is known in the art. In one such embodiment, a sample from a patient described herein is assessed for a KRas$^{G12C}$ mutation using, for example, immunohistochemistry (IHC) or NGS sequencing.

In one embodiment of the methods provided herein a patient is diagnosed having a CR following treatment with a combination therapy according to the methods provided herein. In one embodiment of the methods provided herein a patient is diagnosed having a PR following treatment with a combination therapy according to the methods provided herein. In one embodiment of the methods provided herein a patient is diagnosed having stable disease (SD) following treatment with a combination therapy according to the methods provided herein.

Also provided herein are methods of inhibiting tumor growth or producing tumor regression in a patient described herein by administering a combination therapy described herein. In one embodiment provided herein is a method of inhibiting tumor growth in a patient having a cancer described herein by administering a combination therapy comprising GDC-6036 or a pharmaceutically acceptable salt thereof and inavolisib in one or more cycles (e.g. 21-day or 28-day cycles) as described herein. In one embodiment provided herein is a method of inhibiting tumor growth in a patient having NSCLC or CRC as described herein by administering a combination therapy comprising GDC-6036 or a pharmaceutically acceptable salt thereof and inavolisib in one or more cycles (e.g. 21-day or 28-day cycles) as described herein.

In one embodiment provided herein is a method of producing or improving tumor regression in a patient having a cancer described herein by administering a combination therapy comprising administering GDC-6036 or a pharmaceutically acceptable salt thereof and inavolisib in one or more cycles (e.g. 21-day or 28-day cycles) as described herein. In one embodiment provided herein is a method of producing or improving tumor regression in a patient having NSCLC or CRC described herein by administering a combination therapy comprising administering GDC-6036 or a pharmaceutically acceptable salt thereof and inavolisib in one or more cycles (e.g. 21-day or 28-day cycles) as described herein.

Kits

The combination therapies described herein can be provided as a kit comprising one or more of the agents described herein for administration. In one embodiment, the kit includes GDC-6036 or a pharmaceutically acceptable salt thereof (e.g. GDC-6036 adipate) for administration in combination with inavolisib. In another embodiment, the kit includes GDC-6036 or a pharmaceutically acceptable salt thereof (e.g. GDC-6036 adipate) packaged together with a inavolisib, where the kit comprises separate formulated dosages of each agent.

Also provided herein is an article of manufacture or a kit comprising GDC-6036 or a pharmaceutically acceptable salt thereof (e.g. GDC-6036 adipate) and inavolisib. In some instances, the article of manufacture further comprises one or more package inserts comprising instructions for using the agents described herein to treat or delay progression of a solid tumor (e.g. lung cancer or CRC). In one such embodiment, the cancer is NSCLC.

In some instances, inavolisib and GDC-6036 or a pharmaceutically acceptable salt thereof (e.g. GDC-6036 adipate) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some instances, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some instances, the article of manufacture further includes one or more of another agent (e.g., an additional chemotherapeutic agent or anti-neoplastic agent). Suitable containers for the one or more agents include, for example, bottles, vials, bags and syringes.

Any of the articles of manufacture or kits described herein may include instructions to administer GDC-6036 or a pharmaceutically acceptable salt thereof (e.g. GDC-6036 adipate) and/or inavolisib to a patient in accordance with any of the methods described herein.

Biomarkers

In one embodiment, a patient as described herein must be evaluated for and have a confirmed KRasG12C mutation before administration of a combination therapy as described herein. In one such embodiment, no evaluation for the presence of mutant PIK3CA is performed prior to administration of a combination therapy as described herein.

In one embodiment, the alkylation of KRas$^{G12C}$ by GDC-6036 or a pharmaceutically acceptable salt thereof is measured in the patient. In one such embodiment, the measurement is performed using a sample and tested for alkylation of KRas$^{G12C}$ as provided herein. In another embodiment, assessment of ctDNA biomarkers (e.g., KRas$^{G12C}$) from peripheral blood is performed.

In one embodiment, modulation of KRAS/MAPK target genes (e.g., DUSP6, SPRY4), pathway components (e.g., pERK, pS6), and related biomarkers (e.g., Ki67) through analysis of paired pre-treatment and on-treatment fresh tumor biopsies is performed.

Inavolisib is a selective inhibitor of the Class I PI3Kα isoform (p110α). Without being bound by any particular theory, by inhibiting the phosphorylation of PIP$_2$ to PIP$_3$, inavolisib decreases downstream activation of pathway effectors including AKT, PRAS40, and S6RP, which may serve as PD biomarkers for the treatment with GDC-6036 and inavolisib.

EMBODIMENTS

Provided below are some exemplary embodiments of the invention.

Embodiment 1. A combination therapy comprising:
  (a) GDC-6036 or a pharmaceutically acceptable salt thereof as described herein; and
  (b) inavolisib or a pharmaceutically acceptable salt thereof as described herein.

Embodiment 2. The combination therapy of embodiment 1, wherein GDC-6036 is an adipate salt thereof.

Embodiment 3. The combination therapy of embodiment 1 or 2, wherein GDC-6036 or a pharmaceutically acceptable salt thereof is administered QD according to a dosing regimen comprising one or more cycles.

Embodiment 4. The combination therapy of embodiment 3, wherein GDC-6036 or a pharmaceutically acceptable salt thereof is administered QD on days 1-21 of a dosing regimen comprising one or more 21-day cycles, wherein GDC-6036 or a pharmaceutically acceptable salt thereof is administered orally as a tablet or capsule.

Embodiment 5. The combination therapy of embodiment 3, wherein GDC-6036 or a pharmaceutically acceptable salt thereof is administered QD according to a dosing regimen comprising one or more 28-day cycles, wherein GDC-6036 or a pharmaceutically acceptable salt thereof is administered orally as a tablet or capsule.

Embodiment 6. The combination therapy of any one of embodiments 1-5, wherein GDC-6036 or a pharmaceutically acceptable salt thereof is administered at an amount of about 50 mg-500 mg.

Embodiment 7. The combination therapy of any one of embodiments 1-6, wherein GDC-6036 or a pharmaceutically acceptable salt thereof is administered at an amount of about 100 mg, 200 mg, 300 mg, 400 mg, 500 mg, 600 mg, 700 mg, or 800 mg.

Embodiment 8. The combination therapy of any one of embodiments 1-6, wherein GDC-6036 or a pharmaceutically acceptable salt thereof is administered at an amount of about 100 mg, 200 mg, or 400 mg.

Embodiment 9. The combination therapy of any one of embodiments 1-6, wherein GDC-6036 or a pharmaceutically acceptable salt thereof is administered at an amount of about 200 mg.

Embodiment 10. The combination therapy of any one of embodiments 1-6, wherein GDC-6036 or a pharmaceutically acceptable salt thereof is administered at an amount of about 400 mg.

Embodiment 11. The combination therapy of any one of embodiments 1-10, wherein inavolisib or a pharmaceutically acceptable salt thereof is administered QD according to a dosing regimen comprising one or more cycles.

Embodiment 12. The combination therapy of embodiment 11, wherein inavolisib or a pharmaceutically acceptable salt thereof is administered QD on days 1-21 of a dosing regimen comprising one or more 21-day cycles.

Embodiment 13. The combination therapy of any one of embodiments 1-12, wherein inavolisib or a pharmaceutically acceptable salt thereof is administered QD according to a dosing regimen comprising one or more 28-day cycles.

Embodiment 14. The combination therapy of any one of embodiments 1-13, wherein the dosing regimen comprising a rest period wherein one or both of GDC-6036 and inavolisib is not administered.

Embodiment 15. The combination therapy of any one of embodiments 1-13, wherein inavolisib is administered at an amount of about 3, 6, or 9 mg.

Embodiment 16. The combination therapy of any one of embodiments 1-15, wherein inavolisib is administered at an amount of 6 mg.

Embodiment 17. The combination therapy of any one of embodiments 1-15, wherein inavolisib is administered at an amount of 9 mg.

Embodiment 18. The combination therapy of any one of embodiments 1-17, for use in treating lung cancer comprising a $KRas^{G12C}$ mutation.

Embodiment 19. The combination therapy of embodiment 18, wherein the lung cancer is non-small cell lung carcinoma (NSCLC).

Embodiment 20. The combination therapy of any one of embodiments 1-17, for use in treating colorectal cancer (CRC) comprising a $KRas^{G12C}$ mutation.

Embodiment 21. The combination therapy of any one of embodiments 1-20, wherein the patient is evaluated for the presence of a KRasG12C mutation prior to administration.

Embodiment 22. The combination therapy of any one of embodiments 1-21, wherein no evaluation for the presence of mutant PIK3CA is performed prior to administration.

Embodiment 23. A method of treating lung cancer mediated by a $KRas^{G12C}$ mutation in a patient having such a lung cancer, the method comprising administering an effective amount of a combination therapy comprising:
(a) GDC-6036 or a pharmaceutically acceptable salt thereof as described herein administered QD according to a dosing regimen comprising one or more cycles; and
(b) inavolisib or a pharmaceutically acceptable salt thereof as described herein administered QD according to the dosing regimen comprising one or more cycles.

Embodiment 24. The method of embodiment 23, wherein the lung cancer is NSCLC.

Embodiment 25. The method of embodiment 23 or 24, wherein the lung cancer is adenocarcinoma, squamous-cell lung carcinoma or large-cell lung carcinoma.

Embodiment 26. A method of a solid tumor comprising a KRasG12C mutation in patient having such a cancer, said method comprising administering an effective amount of a combination therapy comprising:
(a) GDC-6036 or a pharmaceutically acceptable salt thereof as described herein administered QD according to a dosing regimen comprising one or more cycles; and
(b) inavolisib or a pharmaceutically acceptable salt thereof as described herein administered QD according to the dosing regimen comprising one or more cycles.

Embodiment 27. The method of embodiment 26, wherein the solid tumor is colorectal cancer (CRC).

Embodiment 28. The method of any one of embodiments 23-27, further comprising:
(a) determining the absence or presence of a KRasG12C mutation in a sample taken from a patient with a suspected diagnosed cancer; and
(b) administering to the patient a combination therapy as described herein comprising an effective amount of GDC-6036 or a pharmaceutically acceptable salt thereof and inavolisib.

Embodiment 29. A method of treating tissue agnostic cancer comprising a KRasG12C mutation in patient having such a cancer, said method comprising administering an effective amount of a combination therapy comprising:
(i) determining the absence or presence of a KRasG12C mutation in a sample taken from a patient with a suspected diagnosed cancer; and
(ii) where the patient sample comprises a KRasG12C mutation, administering an effective amount of a combination therapy comprising:
(a) GDC-6036 or a pharmaceutically acceptable salt thereof as described herein administered QD according to a dosing regimen comprising one or more cycles; and
(b) inavolisib or a pharmaceutically acceptable salt thereof as described herein administered QD according to a dosing regimen comprising one or more cycles.

Embodiment 30. The method of any one of embodiments 23-29, wherein the dosing regimen comprises one or more 21-day cycles.

Embodiment 31. The method of embodiment 30, wherein the dosing regimen comprises a rest period wherein one or both of GDC-6036 and inavolisib is not administered.

Embodiment 32. The method of any one of embodiments 23-29, wherein the dosing regimen comprises one or more 28-day cycles.

Embodiment 33. The combination therapy any one of embodiments 23-32, wherein GDC-6036 is an adipate salt thereof.

Embodiment 34. The method of any one of embodiments 23-33, wherein GDC-6036 or a pharmaceutically acceptable salt thereof is administered orally as a tablet or capsule.

Embodiment 35. The method of any one of embodiments 23-34, wherein GDC-6036 or a pharmaceutically acceptable salt thereof is administered at an amount of about 50 mg-500 mg.

Embodiment 36. The method of any one of embodiments 23-35, wherein GDC-6036 or a pharmaceutically acceptable salt thereof is administered at an amount of about 100 mg, 200 mg, 300 mg, 400 mg, 500 mg, 600 mg, 700 mg, or 800 mg.

Embodiment 37. The method of any one of embodiments 23-36, wherein GDC-6036 or a pharmaceutically acceptable salt thereof is administered at an amount of about 100 mg, 200 mg, or 400 mg.

Embodiment 38. The method of any one of embodiments 23-37, wherein GDC-6036 or a pharmaceutically acceptable salt thereof is administered at an amount of about 200 mg.

Embodiment 39. The method of any one of embodiments 23-37, wherein GDC-6036 or a pharmaceutically acceptable salt thereof is administered at an amount of about 400 mg.

Embodiment 40. The method of any one of embodiments 23-39, wherein inavolisib is administered at an amount of about 3 mg, 6 mg, or 9 mg.

Embodiment 41. The method of any one of embodiments 23-40, wherein inavolisib is administered at an amount of 6 mg.

Embodiment 42. The method of any one of embodiments 23-40, wherein inavolisib is administered at an amount of 9 mg.

Embodiment 43. The method of any one of embodiments 23-42, wherein the patient is not evaluated for the presence of mutant PIK3CA prior to administration.

Embodiment 44. Use of a combination therapy comprising GDC-6036 or a pharmaceutically acceptable salt thereof and inavolisib or a pharmaceutically acceptable salt thereof for the treatment of lung cancer, CRC, or pancreatic cancer as described herein.

Embodiment 45. The use of embodiment 44, wherein the cancer is lung cancer or CRC and further comprises a dosing regimen comprising: (i) administering GDC-6036 or a pharmaceutically acceptable salt thereof QD according to a dosing regimen comprising one or more cycles; and (ii) administering inavolisib QD according to the dosing regimen comprising one or more cycles.

Embodiment 46. Use of a combination therapy comprising GDC-6036 or a pharmaceutically acceptable salt thereof and inavolisib or a pharmaceutically acceptable salt thereof for the manufacture of a medicament for the treatment of lung cancer, CRC, or pancreatic cancer.

Embodiment 47. The use of embodiment 46, wherein the cancer is lung cancer or CRC and further comprises a dosing regimen comprising: (i) administering GDC-6036 or a pharmaceutically acceptable salt thereof QD according to a dosing regimen comprising one or more cycles; and (ii) administering inavolisib QD according to the dosing regimen comprising one or more cycles.

Embodiment 48. The use of embodiment 46, wherein the cancer is CRC and further comprising a dosing regimen comprising: (i) administering GDC-6036 or a pharmaceutically acceptable salt thereof QD according to a dosing regimen comprising one or more 21-day cycles; and (ii) administering inavolisib according to a dosing regimen comprising one or more 21-day cycles.

Embodiment 49. The use of any one of embodiments 44-48, wherein the dosing regimen comprises one or more 21-day cycles.

Embodiment 50. The use of any one of embodiments 44-48, wherein the dosing regimen comprises one or more 28-day cycles.

The following Examples are presented by way of illustration, not limitation.

EXAMPLES

Example 1: Combination of GDC-6036 and Inavolisib

The Kirsten rat sarcoma viral oncogene homolog (KRAS) gene encodes a GTPase that plays a central role in mediating cell growth and survival signaling. Mutations in KRAS that result in amino acid substitutions at glycine 12 (G12), glycine 13 (G13), and glutamine 61 (Q61) are common in tumors and are associated with tumorigenesis and maintenance of aggressive tumor growth (Der et al. Nature 1983; 304(5926):507-13; Parada et al. Nature 1982; 297(5866): 474-8; Santos et al. Nature 1982; 298(5872):343-7; Taparowsky et al. Nature 1982; 300(5894):762-5; Capon et al. Nature 1983; 304(5926): 507-13). The $KRAS^{G12C}$ mutation is prevalent in non-small cell lung cancer (NSCLC), colorectal cancer, and other tumor types (Prior et al. Cancer Res 2012; 72(10):2457-67; Vogelestein et al. Science 2013; 339(6127):1546-58).

GDC-6036 is an oral anti-cancer therapeutic agent that selectively targets $KRAs^{G12C}$, resulting in covalent and irreversible inhibition of $KRAS^{G12C}$. GDC-6036 does not target other mutations in KRAS, the wild-type form of KRAS, or other members of the RAS family. Treatment of $KRAS^{G12C}$-positive cells or tumors with GDC-6036 results in decreased KRAS pathway signaling, suppression of cell/tumor cell growth, and induction of apoptosis.

The in vivo anti-tumor efficacy of GDC-6036 (50 mg/kg, PO, QD) alone or in combination with GDC-0077 (25 mg/kg, PO, QD) in non-small cell lung cancer (NSCLC) and colorectal cancer (CRC) xenograft tumor models harboring a KRas G12C mutation was assessed. Single agent GDC-6036 treatment resulted in near tumor stasis (93% tumor growth inhibition [TGI]), whereas treatment with GDC-0077 resulted in tumor growth inhibition (74% TGI). Improved anti-tumor efficacy was observed with combinations of GDC-6036 and inavolisib (113% TGI).

Mice. Female nude mice that were 9-10 weeks old were obtained from Charles River Laboratory (Hollister, CA) weighing an average of 24.5 g. The mice were housed at Genentech in standard rodent micro-isolator cages and were acclimated to study conditions at least 3 days before tumor cell implantation. Only animals that appeared to be healthy and that were free of obvious abnormalities were used for the study.

Studies. Human non-small lung carcinoma NCI-H2122 cells were obtained from the American Type Culture Collection (Rockville, MD) and harbor a G12C oncogenic mutation in K-RAS. Cells were cultured in vitro, harvested in log-phase growth, and resuspended in Hank's Balanced Salt Solution containing Matrigel (BD Biosciences; San Jose, CA) at a 1:1 ratio. The cells were then implanted subcutaneously in the right lateral thorax of 160 nude mice. Each mouse was injected with 10×10$^6$ cells in a volume of 100 μL. Tumors were monitored until they reached a mean tumor volume of 150-290 mm3. Mice were distributed into 10 groups based on tumor volumes with n=10 mice per group. The mean tumor volume across all groups was 213 mm$^3$ at the initiation of dosing.

Mice were administered vehicles (150 μL 0.5% MC and 100 μL 0.5% MCT), 50 mg/kg GDC-6036 (expressed as free-base equivalents) or 25 mg/kg GDC-0077 (expressed as free-base equivalents) or a combination of GDC-6036 and inavolisib. All treatments were administered on a once daily basis (QD) orally (PO) by gavage for 21 days. The study design is summarized in Table 1.

TABLE 1

| No./Sex | Treatment | Dose Level (mg/kg) | Route | Days of Dosing | Dose Conc. (mg/mL) |
|---|---|---|---|---|---|
| 10/F | Vehicle | 0 | PO | 21 QD | 0 |
| 10/F | GDC-6036 | 50 | PO | 21 QD | 8.33 |
| 10/F | GDC-0077 | 25 | PO | 21 QD | 6.25 |
| 10/F | GDC6036 + GDC-0077 | 50 + 25 | PO | 21 QD | 8.33, 6.25 |

Conc. = concentration;
PO = orally;
QD = once daily
Vehicle controls were 0.5% (w/v) methylcellulose (100 μL) + 0.5% (w/v) methylcellulose; 0.2% Tween80 ™ (150 μL). Dose levels and concentrations are expressed as free-base equivalents and were dosed once daily (QD) for 21 days.

Tumor and body weight measurements. Tumor volumes were measured in two dimensions (length and width) using Ultra Cal-IV calipers (model 54-10-111; Fred V. Fowler Co.; Newton, MA) and analyzed using Excel, version 14.2.5 (Microsoft Corporation; Redmond WA). The tumor volume was calculated with the following formula:

Tumor size (mm$^3$)=(longer measurement×shorter measurement$^2$)×0.5

Anti-tumor responses were noted with partial responses (PRs) being defined as a >50% decrease from the initial tumor volume and complete responses (CRs) being defined as a 100% decrease in tumor volume. Animal body weights were measured using an Adventura Pro AV812 scale (Ohaus Corporation; Pine Brook, NJ). Percent weight change was calculated using the following formula:

Body weight change (%)=[(current body weight/ initial body weight)−1]×100]

Tumor growth analysis. A generalized additive mixed model (GAMM) was employed to analyze transformed tumor volumes over time as this approach addresses both repeated measurements from the same subjects and modest dropouts before end. As tumors generally exhibit exponential growth, tumor volumes were subjected to natural log transformation before analysis. Changes in tumor volumes over time in each group are described by fits (i.e., regression splines with auto-generated 3spline bases) generated using customized functions in R version 3.4.2 (2017-09-28) (R Development Core Team 2008; R Foundation for Statistical Computing; Vienna, Austria) which integrate software from open source packages including lme4, mgcv, gamm4, multcomp, settings, plyr, and several packages from the tidyverse such as magrittr, dplyr, tidyr, and ggplot2.

Analysis of body weights. A generalized additive mixed model (GAMM) was also employed to analyze raw body weights (i.e., grams) over time. After data fitting, raw body weight data at each time point from all individual animals and all group fits were normalized and re-plotted separately in two distinct ways: 1) normalized to the starting weight and reported as a percentage to yield % body weight change and 2) normalized to the maximum weight to date and reported as a percentage to yield % body weight loss.

Figure 2:
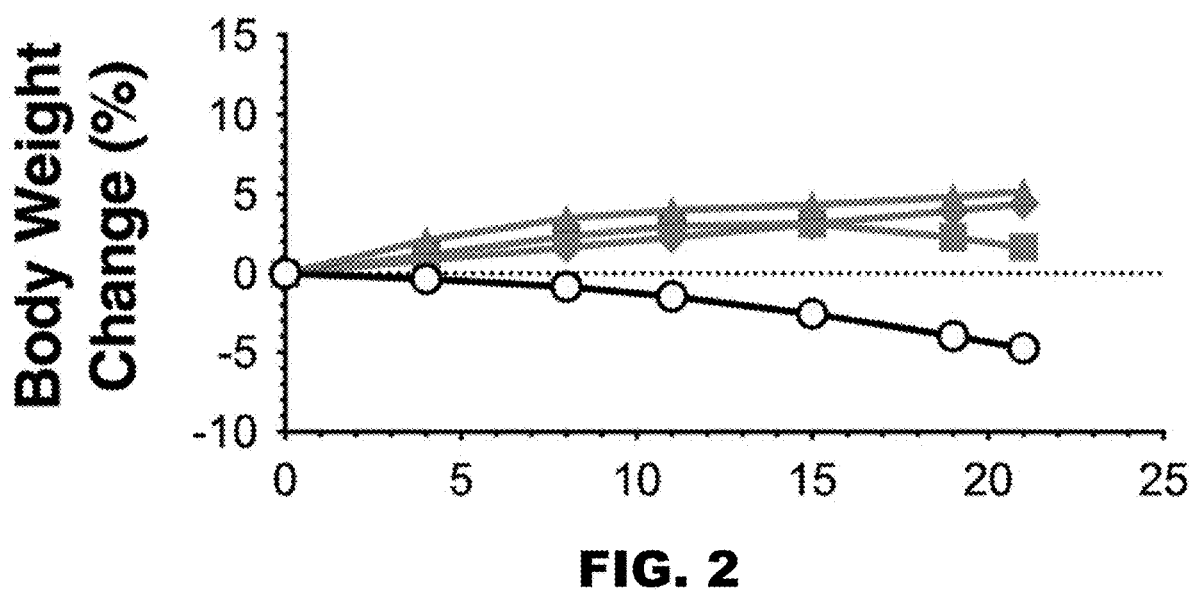
FIG. 2 depicts body weight changes for the administration of GDC-6036 alone, GDC-0077 alone, or the combination of GDC-6036 and inavolisib. All treatments were well-tolerated.
Figure 3A:
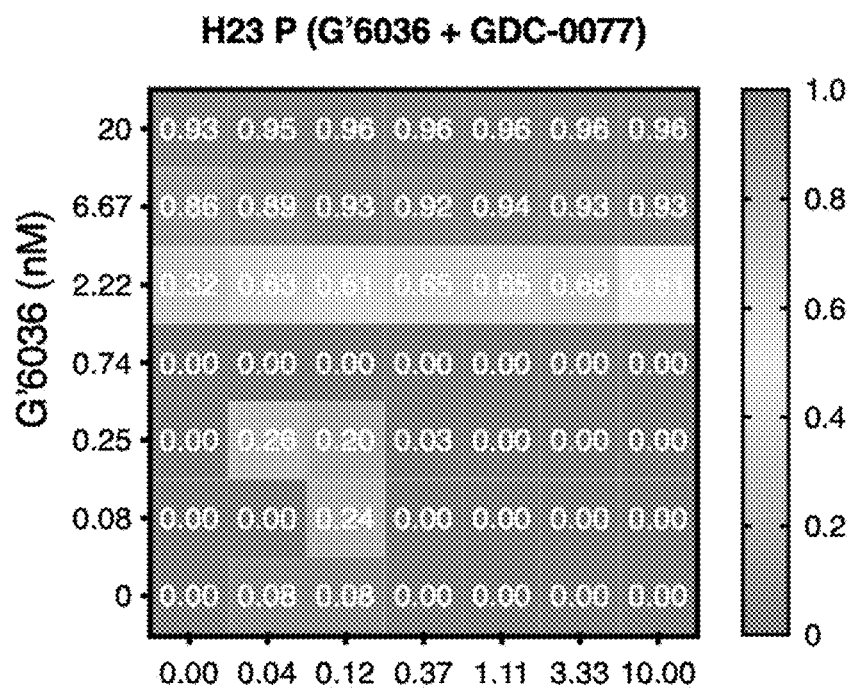
FIG. 3A-FIG. 3H depict synergy plots of the combination of GDC-6036+GDC-0077 for various NSCLC KRas G12C mutant cell lines.
Figure 3B:
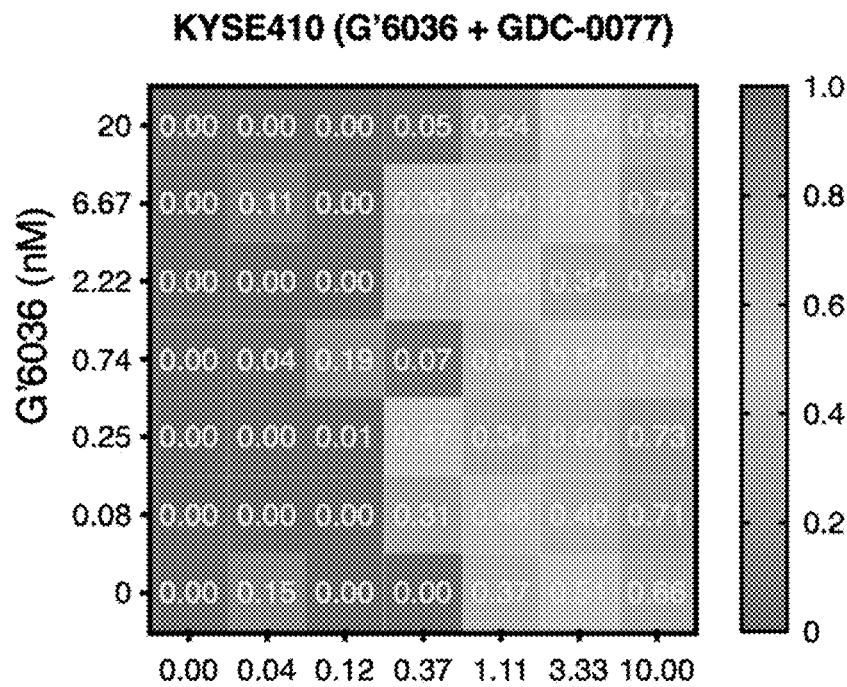
Figure 3C:
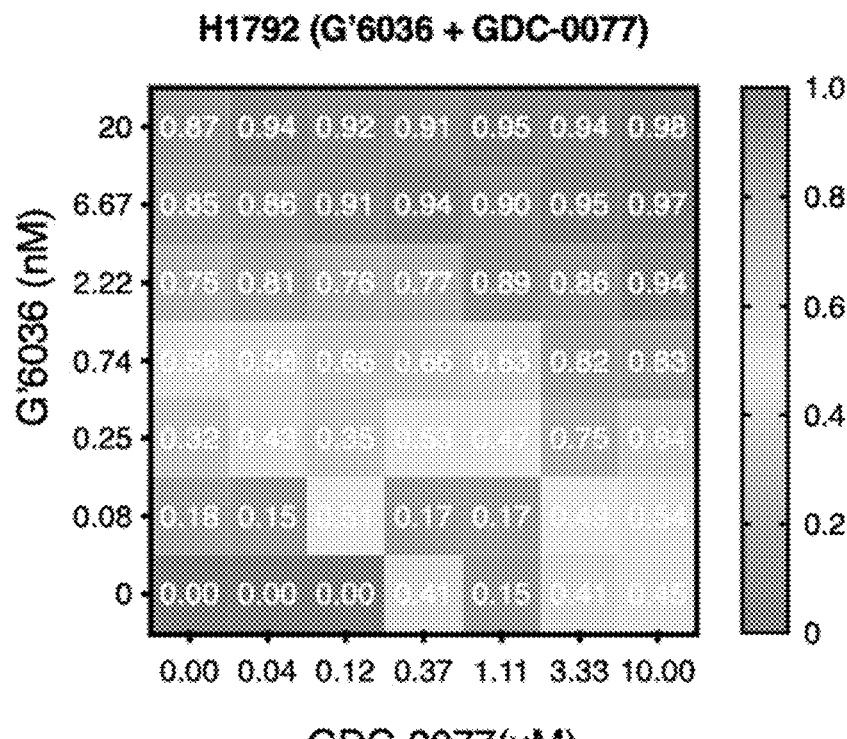
Figure 3D:
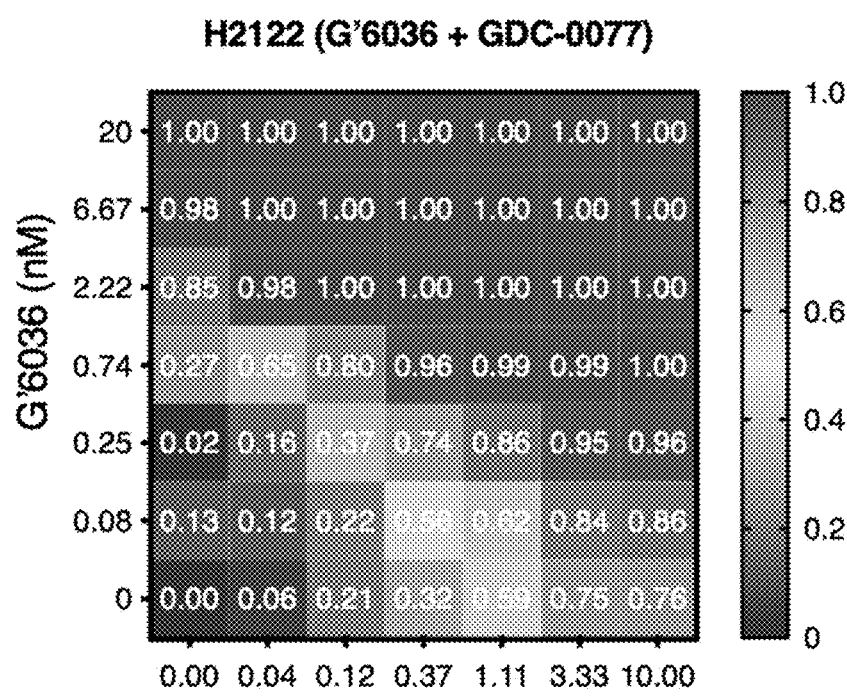
Figure 3E:
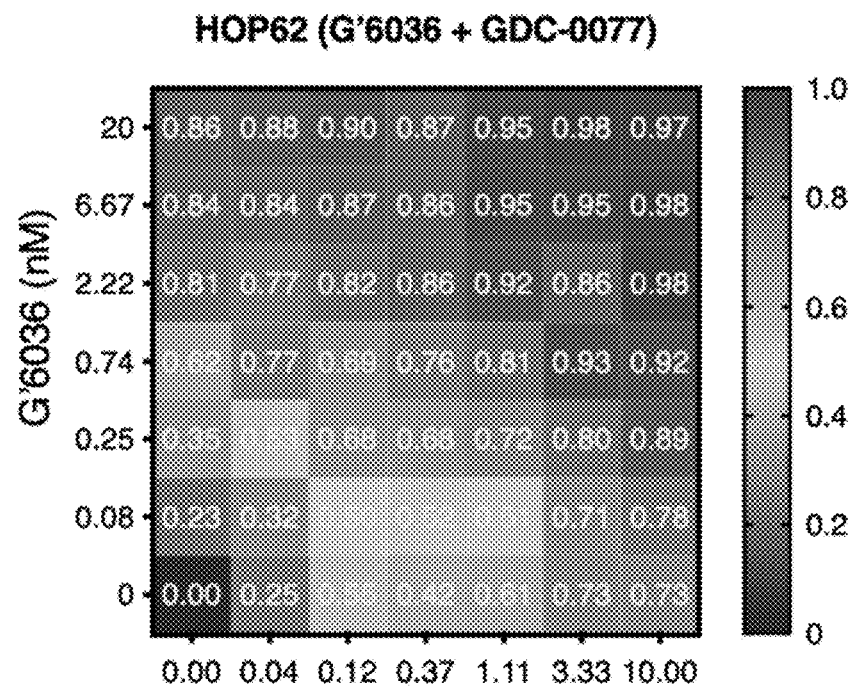
Figure 3F:
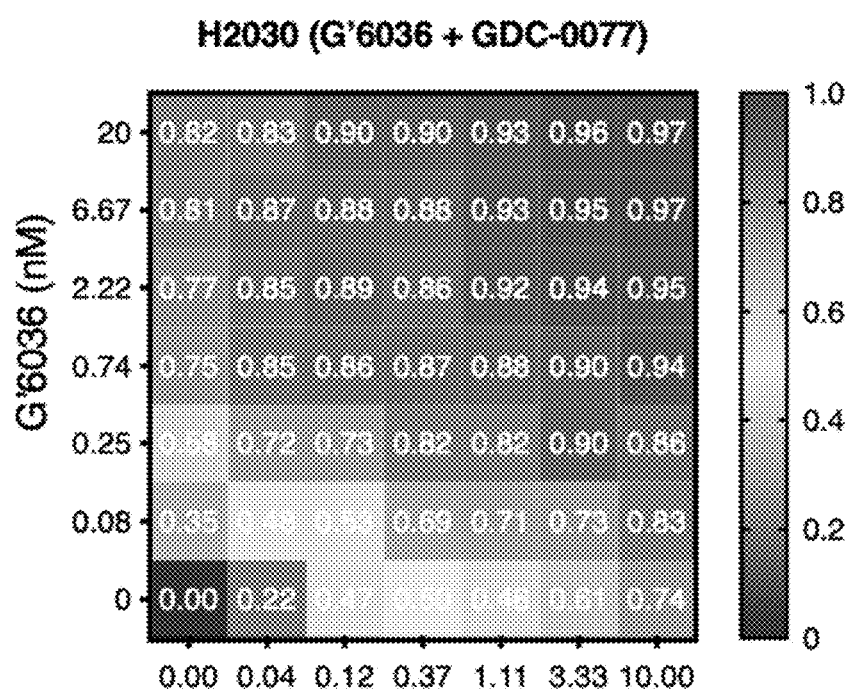
Figure 3G:
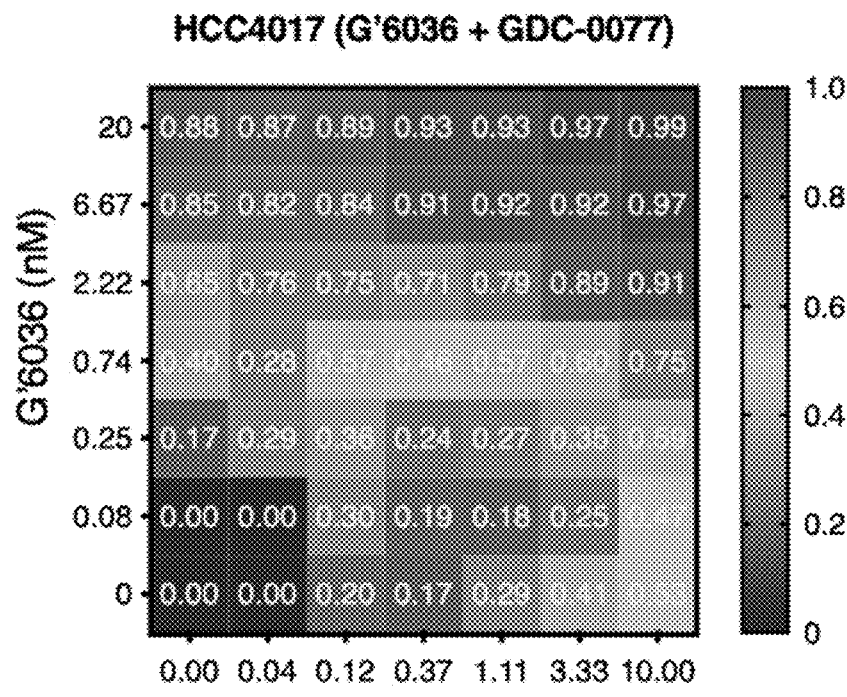
Figure 3H:
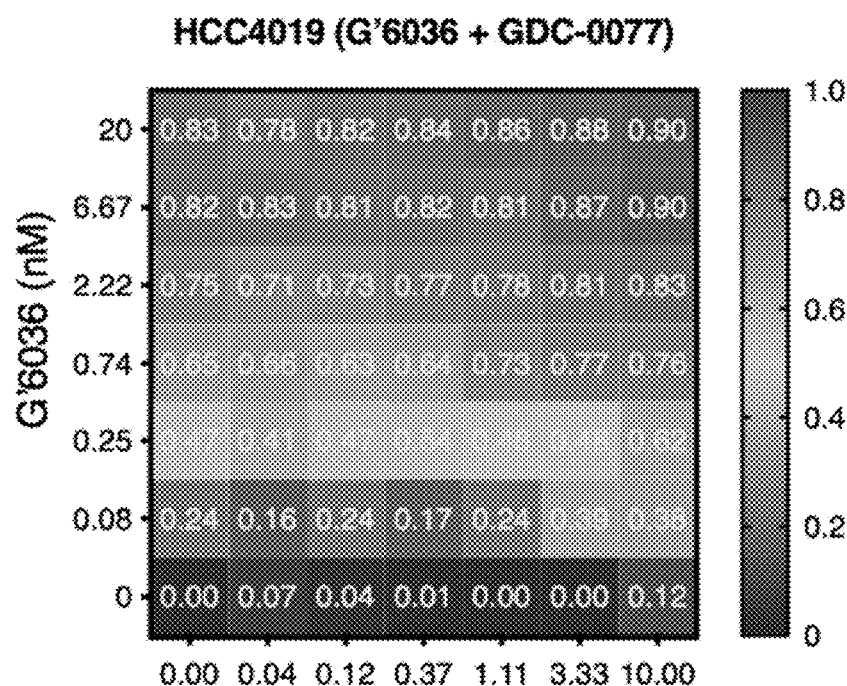

RESULTS. Efficacy and body weights NCI-H2122 xenografts. Anti-tumor efficacy was assessed in nude mice bearing human NCI-H2122 NSCLC xenografts following treatment with GDC-6036 (50 mg/kg, PO, QD) alone, single agent GDC-0077 (25 mg/kg, PO, QD or a doublet combination of GDC-6036 with GDC-0077. The single agent treatments resulted in tumor growth inhibition (TGI), with GDC-6036 resulting in 93% TGI and GDC-0077 resulting in 74% TGI relative to vehicle controls (FIG. 1 and Tables 2 and 3). Improved anti-tumor was observed with combination of GDC-6036 and inavolisib, resulting in 113% TGI and 2/10 PRs (FIG. 1). All treatments were well tolerated, as determined by the percent change in body weights (FIG. 2, and Table 2).

TABLE 2 anti-tumor activity of GDC-6036 alone and in combination with GDC-0077 in human NCI-H2122 NSCLC xenograft tumors

| Treatment | Dose Levels (mg/kg) | TI | PR | CR | % TGI (estimated) | % TGI (lower CI) | % TGI (upper CI) |
|---|---|---|---|---|---|---|---|
| Vehicles | 0 | 10/10 | 0 | 0 | 0 | 0 | 0 |
| GDC-6036 | 50 | 10/10 | 0 | 0 | 93 | 80 | 100 |
| GDC-0077 | 25 | 10/10 | 0 | 0 | 74 | 60 | 85 |
| GDC-6036 + GDC-0077 | 50 + 25 | 10/10 | 0 | 0 | 113 | 107 | 121 |

TI = tumor incidence;
% TGI = percent of tumor growth inhibition;
PR = partial response;
CR = complete response;
CI = confidence interval.
Vehicle controls were 0.5% (w/v) methylcellulose + 0.5% (w/v) methylcellulose; 0.2% Tween80 ™.

Combination of GDC-6036 and inavolisib was further testing in various other NSCLC cell lines harboring a KRasG12C mutation, including H23 P, KYSE410, H1792, H2030, HCC4017, HCC4019, and HOP62. Synergy was observed in concentrations as low as 40 nM in certain cell lines (FIG. 3A-3H).

Figure 4:
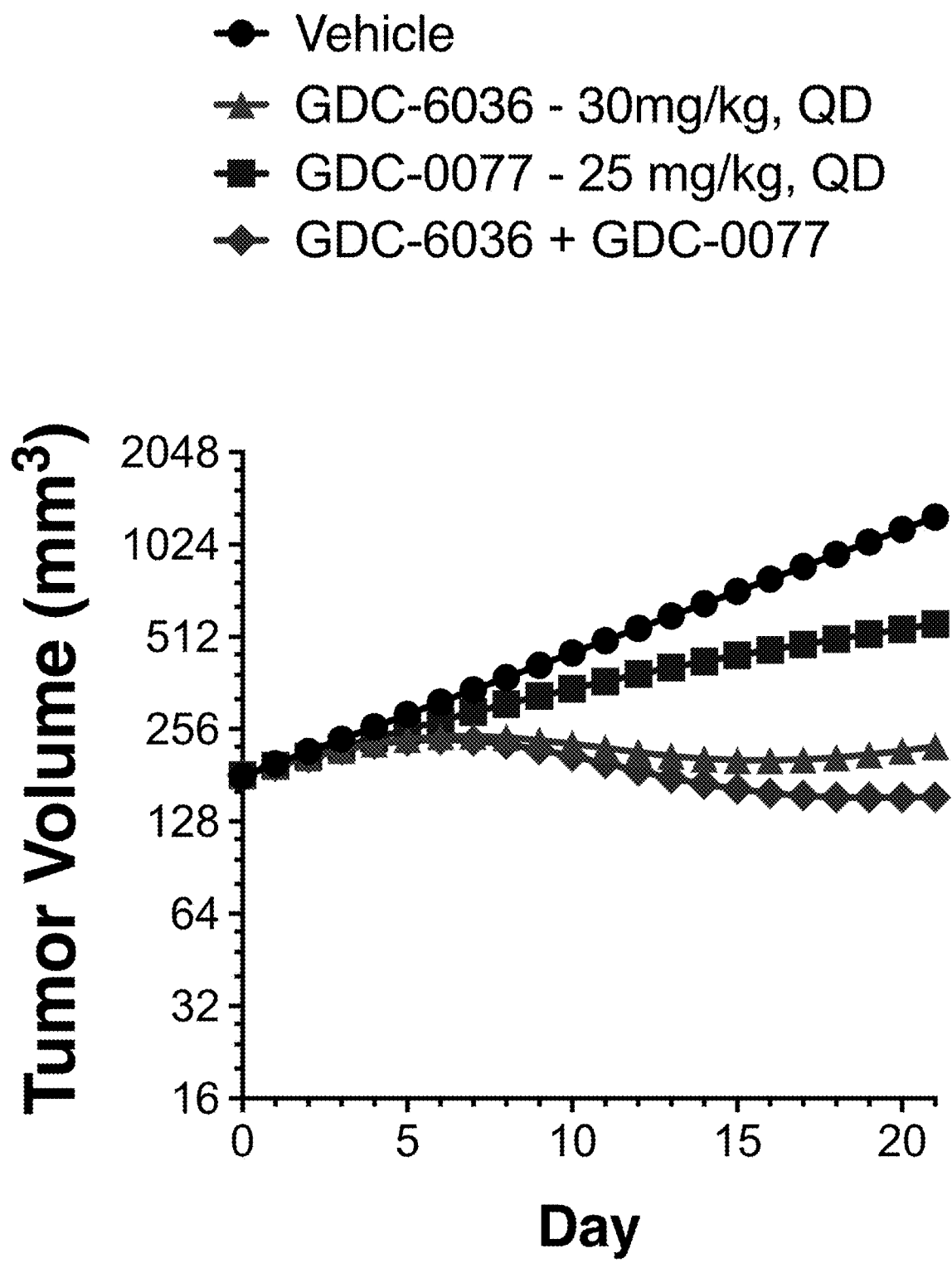
FIG. 4 depicts fitted tumor volumes of treatment with GDC-6036 alone, GDC-0077 alone, or the combination of GDC-6036 and inavolisib in the CR5048 CRC xenograft model.
Figure 5A:
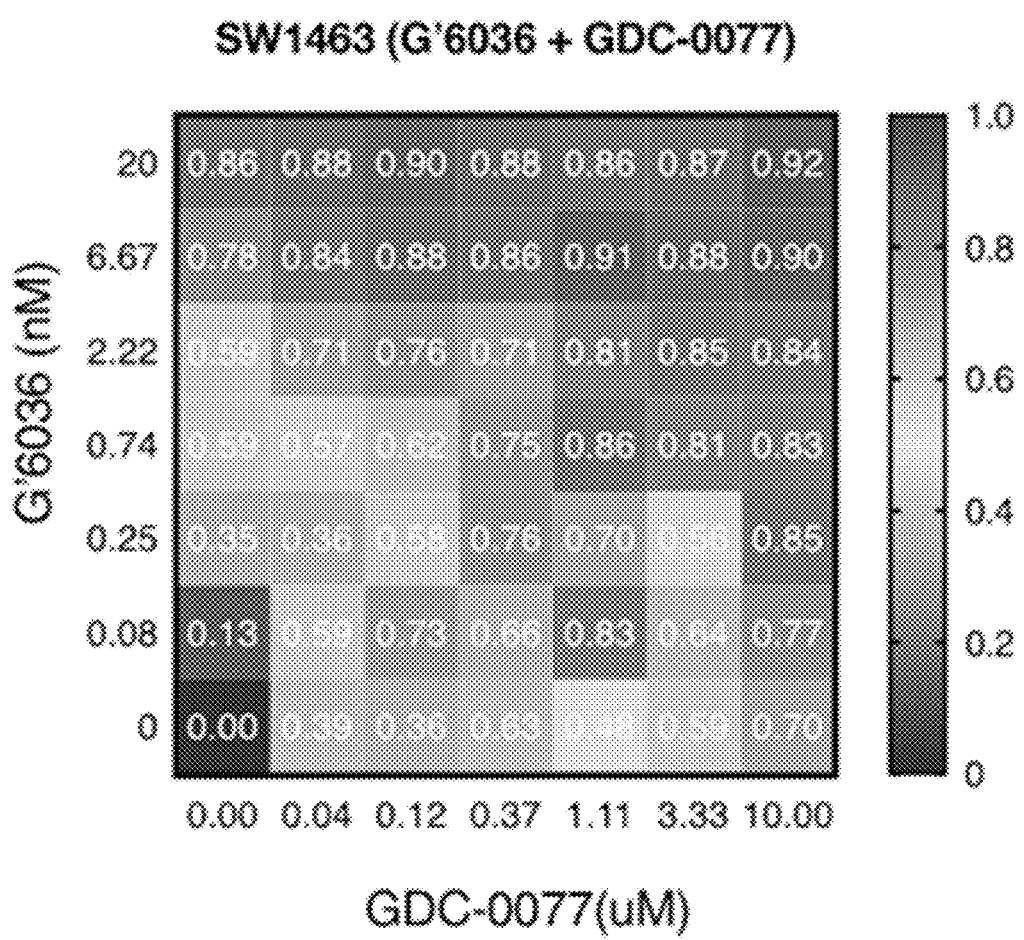
FIG. 5A-FIG. 5C depict synergy plots of the combination of GDC-6036+GDC-0077 for various CRC KRas G12C mutant cell lines.
Figure 5B:
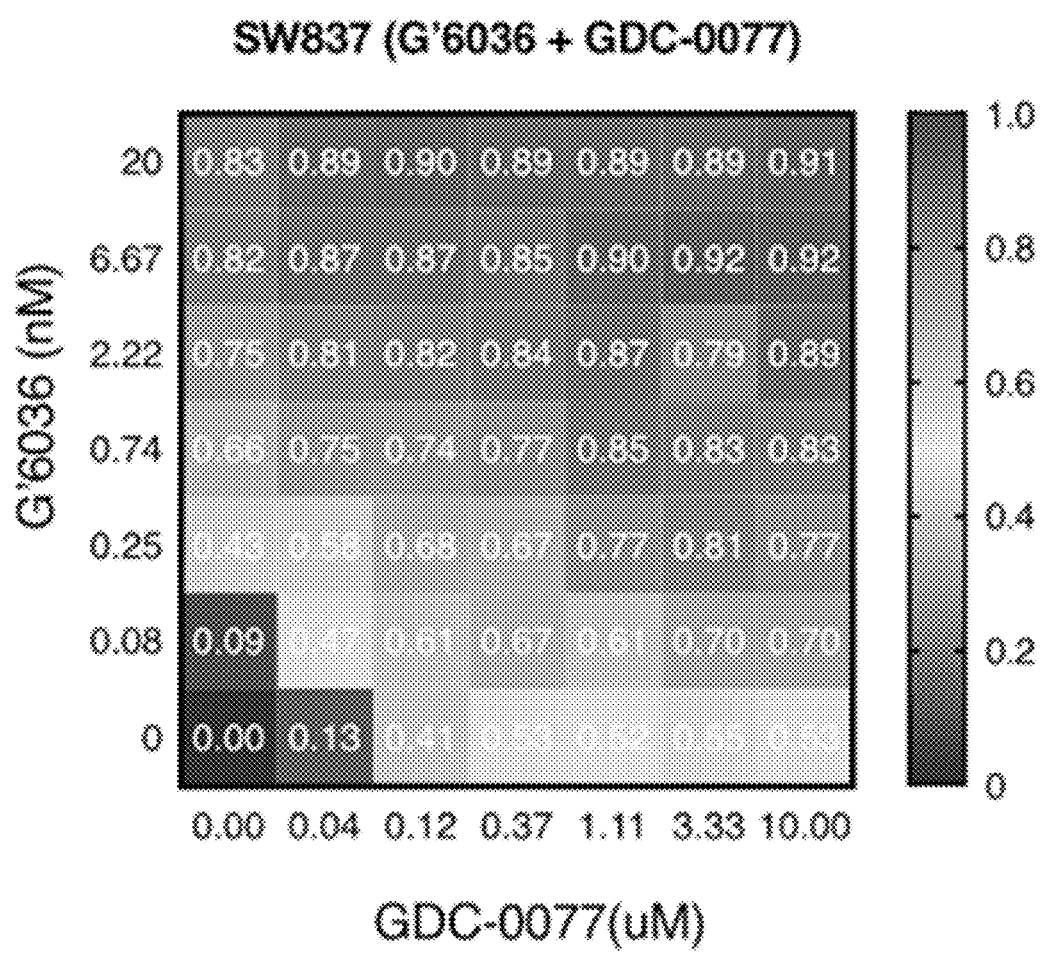
Figure 5C:
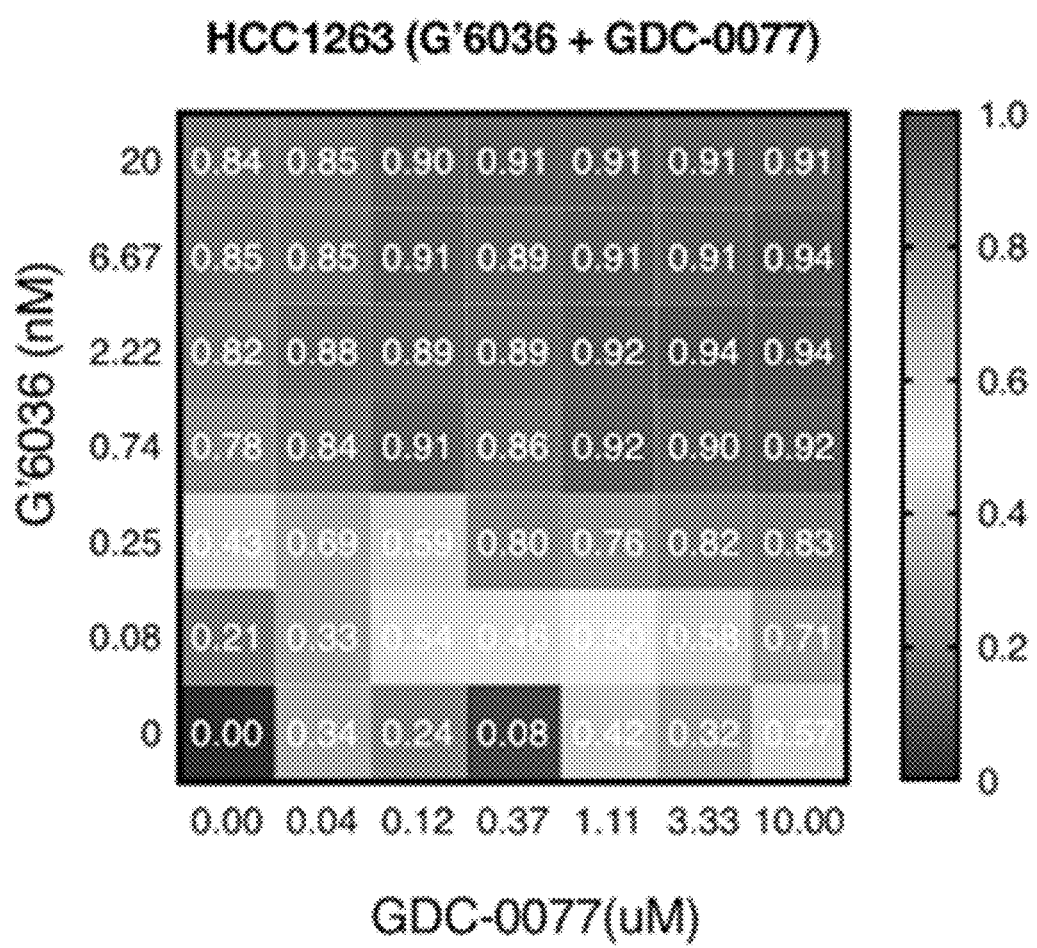

The combination of GDC-6036 and inavolisib was further testing in various CRC cell lines harboring a KRasG12C mutation. The addition of GDC-0077 to GDC-6036 further suppressed cell proliferation, even in the most resistant line (SW1436). See FIG. 5A-5C. Synergistic effect of the combination of GDC-6036 and GDC-0077 was observed in the CR5048 patient-derived xenograft model (FIG. 4 and Table 3).

adverse event. Grade 3 events occurring in more than one patient included ALT increase, diarrhea, anemia, AST increase, and alkaline phosphatase increase. One patient experienced Grade 4 treatment-related ALT increase, and one patient discontinued AMG 510 due to Grade 3 treatment-related ALT and AST increase. While anti-tumor activity was reported, adverse events associated with AMG 510 exist. Patients had a confirmed objective response in 32.2% of patients with NSCLC and the median duration of response was 10.9 months (range, 1.1+ to 13.6) in patients. Median PFS was reported to be 6.3 months (range, 0.0+ to 14.9+) in patients with NSCLC (Hong et al. New Eng J Med 2020; 383:1207-17).

TABLE 3

| Model | Treatment | Dose Levels (mg/kg), Schedule | TI | PR | CR | % TGI (estimated) | % TGI (lower CI) | % TGI (upper CI) |
|---|---|---|---|---|---|---|---|---|
|  | Vehicles | 0 (Vehicles) | 10/10 | 0 | 0 | 0 | 0 | 0 |
| CR5048 | GDC-6036 | 30, PO, QD | 10/10 | 0 | 0 | 90 | 78 | 100 |
| CR5048 | GDC-0077 | 25, PO, QD | 10/10 | 0 | 0 | 52 | 16 | 73 |
| CR5048 | GDC-6036 + GDC-0077 | 30 + 25 | 10/10 | 4 | 0 | 97 | 88 | 106 |

CI = confidence interval;
CR = complete response;
PR = partial response;
QD = once daily;
TI = tumor incidence.
Notes:
% TGI = percent of tumor growth inhibition based on AUC (see Data Analysis section for equation). Vehicle = 0.5% (w/v) methylcellulose Combination anti-tumor efficacy studies performed in various human NSCLC and CRC xenograft tumor models and cell lines harboring KRas G12C mutation demonstrated that the KRAS-G12C inhibitor, GDC-6036, suppresses tumor growth as a single agent. These data demonstrate that combination of the GDC-6036 with GDC-0077 resulted in improved anti-tumor activity relative to single agent observations leading to partial tumor regressions in the human NSCLC and CRC xenograft tumor model.

Example 2

KRAS is the most frequently mutated oncogene in up to 25% of cancers and is associated with resistance to select standard-of-care therapies and overall poor prognosis. Although selective inhibitors have been developed as anti-cancer therapy to target other nodes in the RAS/MAPK pathway, the KRAS oncoprotein was considered undruggable until the recent discovery of the switch II pocket (Ostrem, et al. Nature 2013; 503:548-51). With this finding, covalent small molecule inhibitors aimed at targeting KRAS, and specifically the $KRAS^{G12C}$ mutation, are being evaluated in early clinical development.

Other $KRAS^{G12C}$ inhibitors. AMG 510 (sotorasib) is a small molecule that irreversibly inhibits $KRAS^{G12C}$ by locking it in its inactive GDP-bound state. AMG 510 is currently being investigated in ongoing clinical studies. Patients in those studies received a median of 3 (range, 0 to 11) prior lines of anti-cancer therapies for metastatic disease before entering the study. Overall, treatment-related adverse events were reported in 56.6% of patients; 11.6% of patients experienced a treatment-related Grade 3 or 4 event, and 1.6% of patients experienced a treatment-related serious MRTX849 is a mutant-selective small molecule $KRAS^{G12C}$ inhibitor being evaluated in a clinical study of patients with advanced solid tumors with the $KRAS^{G12C}$ mutation. Data from a total of 17 patients (including 10 patients with NSCLC and 4 patients with CRC), of which 12 patients had undergone at least one on-treatment tumor assessment (including 6 patients with NSCLC and 4 patients with CRC), were reported recently. Most patients had received 3 or more prior anti-cancer regimens before study entry (12 of 17 patients, 71%). The following treatment-related adverse events were reported in >10% of patients: diarrhea, nausea, AST increased, vomiting, fatigue, ALT increased, creatinine increased, abdominal distension, abdominal pain, ALP increased, anemia, decreased appetite, dehydration, dry mouth, dysgeusia, dyspnea, QT prolonged, hypomagnesemia, and rash. Grade 3 events included fatigue, decreased appetite, and dyspnea (1 patient each). Anti-tumor activity with PR was achieved in 3 of 6 patients with NSCLC and 1 of 4 patients with CRC across all dose levels evaluated (Janne et al. AACR-NCI-EORTC International Conference on Molecular Targets and Cancer Therapeutics October 2019).

GDC-6036. The specificity of GDC-6036 for $KRAS^{G12C}$, together with its mechanism of action, leads to potent and irreversible inhibition of $KRAS^{G12C}$, and is expected to enable a broad therapeutic index, maximizing anti-tumor activity while minimizing treatment-related toxicities. Specific therapies aimed at $KRAS^{G12C}$-positive cancer may provide more tolerable and effective treatment options for patients with advanced stage cancers that harbor $KRAS^{G12C}$.

In vitro and in vivo pharmacology studies demonstrate that GDC-6036 is a highly potent and selective covalent inhibitor of $KRAS^{G12C}$, exhibiting over 20,000-fold selectivity in growth inhibition for $KRAS^{G12C}$-positive over $KRAS^{G12C}$-negative cancer cell lines. Mechanism of action studies with GDC-6036 demonstrate that downstream MAPK pathway components such as phosphorylated (p)ERK and pS6, in addition to KRAS target genes such as DUSP6 and SPRY4, are inhibited and apoptosis induction is observed in $KRAS^{G12C}$-positive cancer cell lines. In addition, GDC-6036 has potent single-agent activity and inhibits tumor growth in a number of nonclinical xenograft models of $KRAS^{G12C}$-positive lung tumors. These in vitro and in vivo pharmacology studies support the use of GDC-6036 for the treatment of patients with locally advanced or metastatic $KRAS^{G12C}$-positive solid tumors.

The results of nonclinical toxicology studies completed to date provide a robust characterization of the toxicity profile of GDC-6036 and support the administration of GDC-6036 in patients with cancer. Comprehensive nonclinical toxicity studies were completed to evaluate the potential single and repeat dose oral toxicity, genetic toxicity, phototoxicity, and safety pharmacology of GDC-6036. Because the $KRAS^{G12C}$ mutation is not present in healthy animals, there are no pharmacologically relevant nonclinical species for $KRAS^{G12C}$ inhibition.

Early Phase I clinical data from the ongoing studies of AMG 510 and MRTX849 as single agents have shown that $KRAS^{G12C}$ inhibitors are tolerable and have promising anti-tumor activity in patients with metastatic NSCLC and CRC (Janne et al. 2019; Hong et at. New Eng J Med 2020; 383:1207-17). However, there still remains a great unmet need to improve upon the anti-tumor activity and durability reported in NSCLC and CRC with this class of inhibitors as a single agent while importantly retaining their tolerable safety profile.

Rationale for Combination Therapy. Without being bound by any particular theory, and based on the mechanistic understanding of the RTK-RAS-MAPK pathway, it has been hypothesized that the RAS/MAPK and PI3K/AKT are intricately interconnected signaling pathways and are frequently deregulated in human cancers. Not only do these two pathways share common upstream signaling inputs, but they can play a compensatory role when one or the other is inhibited by targeted therapies. Recent studies have also identified the emergence of genetic alterations in key PI3K pathway components (including PIK3CA and PTEN) when tumors develop resistance to KRAS G12C inhibitors in the clinic (Awad et al. 2021; Zhao et al. 2021), indicating that activation of the PI3K signaling pathway may act as a mechanism of resistance to KRAS G12C inhibitors. As a consequence, simultaneous blockade of both the RAS/MAPK and PI3K/AKT pathways may be required to maximize clinical benefit. The combination of GDC 6036, a highly mutant selective KRAS G12C inhibitor, with inavolisib, a PI3Kα isoform selective inhibitor, may provide a better therapeutic window based upon the single agent safety profiles and selectivity for the oncogenic targets.

Multiple nonclinical studies have shown that combining a KRAS G12C inhibitor with a PI3K inhibitor exhibits broad synergistic effects across multiple in vitro and in vivo models, most of which do not bear deregulating alterations in PI3K pathway components (Misale et al. 2015; Canon et al. 2019; Lou et al. 2019). Mechanistically, the combination of KRAS G12C and PI3K inhibitors is able to simultaneously downregulate both phospho-AKT and phospho-S6RP, resulting in a more robust induction of cell death and inhibition of proliferation compared to a KRAS G12C inhibitor alone (Misale et al. 2018). Consistent with these observations, nonclinical data combining GDC-6036 with inavolisib (Example 1) also showed a synergistic effect with greater tumor reduction in a KRAS G12C—positive cell line and multiple xenograft mouse models compared to the use of either treatment alone.

The starting dose of inavolisib in combination with GDC-6036 will be 6 mg PO QD of each 21-day cycle. The combination of GDC-6036 and inavolisib is anticipated to have acceptable tolerability. Potential overlapping toxicities include GI toxicities and oral mucosal irritation, and are expected to be monitorable and manageable with supportive care and potential dose modifications.

Patients will have locally advanced, recurrent, or metastatic incurable solid tumors that harbor the KRAS G12C mutation and have progressed after at least one available standard therapy; or for whom standard therapy has proven to be ineffective or intolerable, or is considered inappropriate; or for whom a clinical trial of an investigational agent is a recognized standard of care. In addition, patients may have received prior KRAS G12C inhibitor therapy.

Biomarkers. This study will identify and/or evaluate biomarkers that are predictive of response to GDC-6036 as a single agent or in combination with a PI3K inhibitor (i.e., predictive biomarkers), early surrogates of activity, associated with progression to a more severe disease state (i.e., prognostic biomarkers), associated with acquired resistance to $KRAS^{G12C}$ inhibitors (e.g., GDC-6036), associated with susceptibility to developing adverse events or can lead to improved adverse event monitoring or investigation (i.e., safety biomarkers), can provide evidence of GDC-6036 activity in combination with inavolisib (i.e., pharmacodynamic [PD] biomarkers), or can increase the knowledge and understanding of disease biology and drug safety. Corresponding biomarker endpoints include the relationship between exploratory biomarkers in blood, plasma, and tumor tissue and safety, PK, activity, or other biomarker endpoints.

Patients are screened for period of up to 28 days, followed by a treatment period, and a safety follow-up period during which patients will be followed for safety outcomes for a treatment-specific period after their final dose of study drug or until they receive another anti-cancer therapy, whichever occurs first.

In the absence of unacceptable toxicities and unequivocal disease progression as determined by the investigator, patients may continue treatment with GDC-6036.

All patients will be closely monitored for adverse events throughout the study and for a treatment-specific period after the final dose of study treatment or until initiation of another anti-cancer therapy, whichever occurs first. Adverse events will be graded according to the NCI CTCAE v5.0.

Inavolisib is a selective inhibitor of the Class I PI3Kα isoform (p110α). By inhibiting the phosphorylation of $PIP_2$ to $PIP_3$, inavolisib decreases downstream activation of pathway effectors including AKT, PRAS40, and S6RP, which may serve as PD biomarkers for the treatment with GDC-6036 and inavolisib.

$KRas^{G12C}$ Mutation Status from Tissue and Circulating Tumor DNA Assessments. Approximately 12% of NSCLC, 4% of CRC, 2% of pancreatic cancers, and many other solid tumors (prevalence ≤4% in each) harbor the $KRas^{G12C}$ mutation. GDC-6036 is a potent and highly selective inhibitor that targets $KRas^{G12C}$, but not other mutations in KRAS, the wild-type form of KRAS, or other members of the RAS family. Therefore, only patients with tumors harboring the $KRas^{G12C}$ mutation are eligible for administration of combination therapies described herein. KRAS mutation status may be determined using the FoundationOne® CDx (F1CDx) assay, a U.S. Food and Drug Administration (FDA)-approved broad companion diagnostic (CDx) assay, FoundationOne® Liquid CDx (F1L CDx) assay, as well as other FDA approved (FDA 2020) or well-validated laboratory developed tests performed in a Clinical Laboratory Improvement Amendments (CLIA)-validated or equivalently certified laboratory. Previous studies indicate that occurrence of the KRas$^{G12C}$ mutation is an early event (Jamal-Hanjani et al. N Engl J Med 2017; 376:2109-21), suggesting that analysis of archival tissue is a sufficient surrogate for selection of patients with KRas$^{G12C}$-positive tumors for GDC-6036 treatment.

Pharmacodynamic Pathway Modulation. GDC-6036 is a KRas$^{G12C}$ inhibitor that suppresses downstream MAPK signaling by alkylation of KRas$^{G12C}$, thereby locking it in its inactive GDP-bound state. In nonclinical models, the level of KRas$^{G12C}$ alkylation by GDC-6036 and the extent of MAPK pathway suppression correlate with response to GDC-6036. Pre-treatment and on-treatment tumor tissue collection will enable an assessment of the correlation of MAPK pathway suppression and anti-tumor activity with GDC-6036 treatment. The extent of MAPK pathway suppression can be assessed using RNA analysis of MAPK target genes (e.g., DUSP6, SPRY4) or immunohistochemistry (IHC) analysis of phosphorylated downstream markers (e.g., pERK, pS6). In addition, on-treatment tumor tissue biopsies may enable direct assessment of the level of KRas$^{G12C}$ alkylation by GDC-6036. The assessment of these PD biomarkers may inform future dose selection.

Sequencing of Genes Related to Resistance to GDC-6036. DNA sequencing techniques, such as targeted next-generation sequencing (NGS) and whole exome sequencing, may offer a unique opportunity to identify biomarkers of response and/or resistance to GDC-6036. Sequencing of cancer-related genes may result in the identification of de novo and acquired mechanisms of resistance to GDC-6036.

Protein, RNA, and DNA Analysis. In addition to mutational activation of proteins, expression levels of RNA or alterations in DNA may also modulate the activity of signaling pathways. RNA profiling of tumors will allow intrinsic subtyping of patients enrolled in the study. Analysis of the potential association between subtypes and patient outcome may identify subpopulations of patients who are most likely to respond to GDC-6036.

Plasma Sample for Somatic Tumor Mutation Analysis and Other Biomarkers. There is increasing evidence that cell-free DNA obtained from blood specimens of patients with cancer contains ctDNA, which is representative of the DNA and mutational status of cells in the tumor (Diehl et al. 2008; Maheswaran et al. 2008). Assays have been validated to detect cancer-related mutations (e.g., KRAS) from plasma. Results of these assays may be correlated with the mutational status determined from analysis of tumor specimens. The use of ctDNA to monitor response to treatment is an area of great interest, and could allow for an early, non-invasive, and quantifiable method for use in the clinical setting to identify candidates for specific therapies and monitoring of mutation status of the cancer over time (Wan et al. Nat Rev Cancer 2017; 17:223-38). Analysis of ctDNA collected at various times during study treatment and after a patient progresses on GDC-6036 may help to identify mechanisms of response and acquired resistance to study treatment.

Blood Sample for Next-Generation Sequencing. Next-generation sequencing (NGS) technologies can generate a large quantity of sequencing data. Tumor DNA can contain both reported and unreported chromosomal alterations because of the tumorigenesis process. To help control for sequencing calls in previously unreported genomic alterations, a predose blood sample will be taken to determine whether the alteration is somatic.

Inclusion Criteria. Patients must meet the following criteria for study entry:

Age ≥18 years;

Evaluable or measurable disease per RECIST v1.1;

Eastern Cooperative Oncology Group (ECOG) performance status of 0 or 1;

Life expectancy of ≥12 weeks;

Adequate hematologic and organ function within 14 days prior to initiation of study treatment, defined by the following:

Absolute neutrophil count ≥1200/μL;

Hemoglobin ≥9 g/dL;

Platelet count ≥100,000/μL;

Total bilirubin ≤1.5×ULN;

Serum albumin ≥2.5 g/dL;

AST and ALT ≤2.5×ULN with the following exception: Patients with documented liver metastases may have AST and/or ALT ≤5.0×ULN.

Serum creatinine ≤1.5×ULN or creatinine clearance ≥50 mL/min on the basis of the Cockcroft-Gault glomerular filtration rate estimation:
(140-age)×(weight in kg)×(0.85 if female) 72×(serum creatinine in mg/dL)

For women of childbearing potential: Agreement to remain abstinent (refrain from heterosexual intercourse) or use contraception, and agreement to refrain from donating eggs;

For men who are not surgically sterile: Agreement to remain abstinent (refrain from heterosexual intercourse) or use contraception, and agreement to refrain from donating sperm;

Confirmation of biomarker eligibility: Valid results from either central testing of blood or local testing of blood or tumor tissue documenting the presence of the KRas$^{G12C}$ mutation (e.g. validated polymerase chain reaction (PCR)-based or NGS assay performed at a CLIA or equivalently certified laboratory).

Additional inclusion criteria

Histologically documented locally advanced, recurrent, or metastatic incurable malignancy.

Disease that has progressed after at least one available standard therapy; or for whom standard therapy has proven to be ineffective or intolerable; or for whom a clinical trial of an investigational agent is a recognized standard of care Fasting glucose ≤140 mg/dL and glycosylated hemoglobin (HbA1c)<7%

Patients may have received prior treatment with a KRas$^{G12C}$ specific inhibitor.

Histologically documented, locally advanced, recurrent, or metastatic incurable NSCLC (may include single-agent or combination therapy with an investigational or approved PD-L1/PD-1 inhibitor)

General Exclusion Criteria. Patients who meet any of the following criteria will be excluded:

Inability or unwillingness to swallow pills;

Inability to comply with study and follow-up procedures;

Malabsorption syndrome or other condition that interferes with enteral absorption;

Known and untreated, or active central nervous system (CNS) metastases;

Patients with a history of treated CNS metastases provided they meet all of the following criteria:

Measurable or evaluable disease outside the CNS;
No history of intracranial hemorrhage or spinal cord hemorrhage;
No ongoing requirement for corticosteroids as therapy for CNS metastases, with corticosteroids discontinued for 2 weeks prior to administration of an agent described herein and no ongoing symptoms attributed to CNS metastases;
No stereotactic radiation within 7 days or whole-brain radiation within 14 days prior to Day 1 of Cycle 1;
No evidence of interim progression between the completion of CNS-directed therapy and the screening radiographic study;
Leptomeningeal disease or carcinomatous meningitis;
Uncontrolled pleural effusion, pericardial effusion, or ascites requiring recurrent drainage procedures biweekly or more frequently;
Indwelling pleural or abdominal catheters may be allowed, provided the patient has adequately recovered from the procedure, is hemodynamically stable and symptomatically improved;
Any active infection that could impact patient safety, or serious infection requiring IV antibiotics within 7 days prior to Day 1 of Cycle 1;
Clinically significant history of liver disease, including viral or other hepatitis, current alcohol abuse, or cirrhosis;
Known HIV infection;
Uncontrolled hypercalcemia (>1.5 mmol/L ionized calcium or calcium >12 mg/dL or corrected serum calcium ≥ULN) or symptomatic hypercalcemia requiring continued use of bisphosphonate therapy or denosumab;
Significant traumatic injury or major surgical procedure within 4 weeks prior to Day 1 of Cycle 1;
Patients with chronic diarrhea, short bowel syndrome or significant upper gastrointestinal surgery including gastric resection, a history of inflammatory bowel disease (e.g., Crohn's disease or ulcerative colitis) or any active bowel inflammation (including diverticulitis);
Treatment with chemotherapy, immunotherapy, or biologic therapy as anti-cancer therapy within 3 weeks prior to administration of an agent described herein, or endocrine therapy within 2 weeks prior administration of an agent described herein, except for the following:
Hormonal therapy with gonadotropin-releasing hormone (GnRH) agonists or antagonists for endocrine sensitive cancers (e.g., prostate, endometrial, hormone receptor-positive breast cancer);
Kinase inhibitors, approved by regulatory authorities, may be used up to 2 weeks prior to initiation of study treatment;
Treatment with an investigational agent within 3 weeks or five half-lives prior to administration of an agent described herein, whichever is shorter.
Radiation therapy (other than palliative radiation to bony metastases and radiation to CNS metastases) as cancer therapy within 4 weeks prior to administration of an agent described herein;
Palliative radiation to bony metastases within 2 weeks prior to administration of GDC-6036;
Adverse events from prior anti-cancer therapy that have not resolved;
History of other malignancy within 5 years prior to screening;
History of or active clinically significant cardiovascular dysfunction, including:
History of stroke or transient ischemic attack within 6 months prior to administration of an agent described herein;
History of myocardial infarction within 6 months prior to administration of an agent described herein;
New York Heart Association Class III or IV cardiac disease or congestive heart failure requiring medication
Uncontrolled arrhythmias, history of or active ventricular arrhythmia requiring medication;
Coronary heart disease that is symptomatic or unstable angina;
Congenital long QT syndrome or QT interval corrected through use of Fridericia's formula (QTcF) >470 ms;
Current treatment with medications known to prolong the QT interval;
Pregnant or breastfeeding, or intending to become pregnant during the study or within 6 months after the final dose of GDC-6036; or
History of idiopathic pulmonary fibrosis, organizing pneumonia (e.g., bronchiolitis obliterans), drug-induced pneumonitis, or idiopathic pneumonitis, or evidence of active pneumonitis on screening chest computed tomography (CT) scan;
Other exclusion criteria
Type 1 and Type 2 diabetes requiring anti-hyperglycemic medication
Any concurrent ocular or intraocular condition (e.g., cataract or diabetic retinopathy) that, in the opinion of the investigator and/or study ophthalmologist, would require medical or surgical intervention during the study period to prevent or treat vision loss that might result from that condition
Active inflammatory (e.g., uveitis or vitritis) or infectious (e.g., conjunctivitis, keratitis, scleritis, or endophthalmitis) conditions in either eye or history of idiopathic or autoimmune-associated uveitis in either eye
Patients requiring any daily supplemental oxygen
History of or active inflammatory disease (e.g., Crohn's disease or ulcerative colitis) or any active bowel inflammation (including diverticulitis) including Patients currently receiving immunosuppressants (e.g., sulfasalazines) are considered to have active disease and are, therefore, ineligible.
History of prior significant toxicity related to another PI3K or mTOR inhibitor requiring discontinuation of treatment
Study Treatment Formulation, Packaging, and Handling.

GDC-6036 will be supplied as an active pharmaceutical ingredient (API) powder-in-capsule (PIC) formulation in three strengths: 5 mg, 25 mg, and 100 mg (free base equivalent). GDC-6036 drug products should be stored at or below 86° F. (30° C.) and protected from moisture.

For GDC-6036 doses to be administered at home, a sufficient number of capsules or tablets should be dispensed to the patient to last until the next visit or through one cycle. Patients will self-administer GDC-6036 as provided herein, except when patients visit a clinic. Patients should take GDC-6036 at approximately the same time each day unless otherwise instructed. Patients will be instructed as to the number and strength of capsules or tablets to take, according to their assigned dose level and schedule.

Unless otherwise instructed, GDC-6036 should be taken on an empty stomach, i.e., food should be avoided at least 2 hours before as well as 1 hour after the dose is administered. There are no restrictions on water intake. Importantly, GDC-6036 capsules or tablets will be swallowed whole (not chewed) with a minimum of 240 mL (8 fluid ounces) of water. If a patient misses any dose of GDC-6036 or vomits up a capsule or tablet, the patient should be instructed to skip that dose and resume dosing with the next scheduled dose. Missed doses will not be made up.

Inavolisib will be supplied by the Sponsor as tablets in two strengths: 3 mg and 9 mg. Inavolisib will be administered PO QD starting at 6 mg in 21-day cycles, and will not exceed the single agent MTD of 9 mg QD. Inavolisib may be administered at the same time as GDC-6036, with sips of water in between. Patients will self-administer inavolisib except on study visit days when inavolisib will be administered in the clinic.

Patients should take inavolisib at approximately the same time each day without regard to the timing of administration of food unless otherwise instructed. If a patient misses any dose of inavolisib (not taken within 6 hours after the scheduled dosing time) or vomits up a tablet, the patient should skip that dose, document it and resume dosing with the next scheduled dose.

Concomitant Therapy. Concomitant therapy consists of any medication (e.g. prescription drugs, over-the-counter drugs, vaccines, herbal or homeopathic remedies, nutritional supplements) used by a patient in addition to an agent described herein from 7 days prior to the first administration of at least one agent described herein to the last administration of at least one agent described herein.

Permitted Therapy. Patients may take (a) anti-seizure medications or warfarin; (b) oral contraceptives or other allowed maintenance therapy as specified in the eligibility criteria; (c) anti-emetics and anti-diarrheal medications should not be administered prophylactically before initial treatment with study drug; (d) pain medications; (e) bisphosphonate and denosumab therapy for bone metastases or osteopenia or osteoporosis; or multivitamins, calcium, and vitamins C, D, and E supplements are allowed.

Precautionary Therapy. Medications Given with Precaution due to Effects Related to CYP Enzymes and GDC-6036 include, for example, (1) Strong/moderate CYP3A4 inhibitors, including, but not limited to, the following: atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements; (2) Strong/moderate CYP3A4 inducers, including, but not limited to, the following: rifampin, carbamazepine, phenytoin, oxcarbazepine, phenobarbital, efavirenz, nevirapine, etravirine, modafinil, hyperforin (St. John's Wort), and cyproterone. The use of full-dose oral or parenteral anticoagulants for therapeutic purpose as long as the INR and/or aPTT is within therapeutic limits (according to institution standards) within 14 days prior to administration of any agent described herein and the patient has been on a stable dose of anticoagulants for 1 week prior to initiation of study treatment. The lists of medications are not intended to be comprehensive.

Coumarins (Coumadine®, warfarin) are strongly discouraged during therapy. If the patient requires anticoagulation therapy, then the use of low molecular-weight heparin instead of coumarins is recommended, where clinically feasible. If there is no clinically feasible alternative to coumarins, frequent monitoring of INR and prothrombin time must be performed.

Prohibited Therapy. Use of the following concomitant therapies is prohibited during and for at least 7 days prior to the first administration of an agent described herein:

Investigational therapy within 3 weeks or five half-lives prior to the first administration of an agent described herein, whichever is shorter;

Concomitant therapy intended for the treatment of cancer whether approved by the FDA or experimental, including chemotherapy, radiotherapy, immunotherapy, biologic therapy, herbal therapy, or hormonal therapy except for the following:

Hormonal therapy with gonadotropin-releasing hormone (GnRH) agonists or antagonists for endocrine sensitive cancers (e.g. prostate, endometrial, hormone receptor-positive breast cancer);

Hormone replacement therapy or oral contraception.

Radiotherapy for unequivocal progressive disease with the exception of new brain metastases in the setting of systemic response: patients who have demonstrated control of their systemic disease (defined as having received clinical benefit [i.e., a PR, CR, or SD for ≥3 months]), but who have developed brain metastases that are treatable with radiation, will be allowed to continue to receive therapy with GDC-6036 during the study until they either experience systemic progression of their disease and/or further progression in the brain (based on investigator assessments);

Quinidine or other anti-arrhythmic agents;

Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1

Cautionary Risks

Strong CYP3A4 inhibitors, including, but not limited to, the following: atazanavir, ritonavir, indinavir, nelfinavir, saquinavir, clarithromycin, troleandomycin, itraconazole, ketoconazole, voriconazole, posaconazole, conivaptan, diltiazem, nefazodone, and mibefradil Strong CYP3A4 inducers, including, but not limited to, the following: rifampin, carbamazepine, phenytoin, oxcarbazepine, phenobarbital, nevirapine, hyperforin (St. John's Wort), and cyproterone Inhibitors of P-gp, including, but not limited to: ritonavir, cyclosporine, verapamil, erythromycin, ketoconazole, itraconazole, quinidine, elacridar, and valspodar Inhibitors of BCRP, including, but not limited to: curcumin, cyclosporine A, eltrombopag Risks Associated with GDC-6036. Administration of GDC-6036 has been associated diarrhea, nausea, vomiting, and minimal to mild transaminase elevation. Other potential risks include oral mucosal irritation.

Risks Associated with inavolisib. On the basis of the established class effects of PI3K and mTOR inhibitors in patients with cancer, as well as nonclinical data and clinical experience with inavolisib, hyperglycemia, stomatitis/oral mucositis, rash, diarrhea/colitis, and pneumonitis are safety concerns for inavolisib. Given that these adverse events may require either dose interruptions and/or dose reductions or may have the potential to cause life-threatening conditions, close monitoring and a robust risk-mitigation strategy is warranted.

Hyperglycemia—Effects on glucose and/or insulin metabolism are a known effect with PI3K inhibitors. Increased glucose was observed in rat and dog toxicology studies at all doses tested and appeared to be dose dependent. Hyperglycemia has been reported in patients receiving inavolisib and is an identified risk of inavolisib. Thus, patients with Type I diabetes or Type II diabetes requiring medications and patients with elevated fasting glucose at baseline (fasting plasma glucose >140 mg/dL or HbA$_{1c}$≥7%) will be excluded. Fasting glucose levels will be assessed at baseline, and fasting glucose levels will be monitored. Patients should be advised to report symptoms associated with hyperglycemia such as polydipsia, polyuria, polyphagia, blurry vision, or symptoms associated with acidosis such as rapid or shallow breathing, confusion, fatigue, headache, or drowsiness. Patients shall be given as a first-line agent for the management of hyperglycemia, metformin.

Stomatitis and Oral Mucositis. Treatment-related stomatitis/oral mucositis has been reported with the use of inavolisib. Patients should be advised to report symptoms immediately. Intervention should begin at the earliest signs of oral mucosal inflammation. If locally available, a compounded alcohol-free mouthwash of dexamethasone (0.5 mg in 5 mL) is recommended for prophylaxis or treatment of stomatitis/mucositis. As per the SWISH study (Rugo et al. 2017), patients may use 4 times daily for 8 weeks (10 mL swished for 2 minutes and spat) started concurrently with study treatment, and/or used reactively with the first appearance of symptoms. Additional mouthwash formulations (e.g., combinations of local anesthetic, antihistamine, corticosteroid, antacid, antifungal, and/or antibiotics) or topical corticosteroids (e.g., triamcinolone acetonide 0.05%-0.5%, fluocinolone acetonide 0.025%-0.05%, clobetasol propionate 0.025%) may be implemented. Patients should avoid alcohol, hydrogen peroxide, iodine, or thyme-containing products, as they may exacerbate the condition. They should also avoid harsh mouthwashes (e.g., Listerine®). Diet should be modified (e.g., avoidance of spicy foods).

Gastrointestinal Toxicities. In the 4-week toxicology study of inavolisib in dogs, GI inflammation was observed. Patients with inflammatory bowel disease, such as Crohn's disease or ulcerative colitis, and active bowel inflammation (e.g., diverticulitis) will be excluded. GI effects will be closely monitored by interval history and physical examination. Development of abdominal pain, nausea, vomiting, clinically significant changes in stool (e.g., diarrhea, bloody stools) may necessitate more frequent monitoring, and study drug may be held if symptoms are prohibitive for normal function. Clinical evaluation for infectious (e.g., *Clostridium difficile*, enteric bacteria, and cytomegalovirus) or inflammatory (e.g., inflammatory colitis) etiologies for diarrhea should be conducted.

Skin Disorders. Treatment-related rash has been reported for other PI3K inhibitors in clinical studies and is commonly manifested as a maculo-papular rash with or without pruritus. Rash and other dermatologic events should be closely monitored and managed per standard of care.

Other potential risks for inavolisib:

Lung Inflammation/Pneumonitis. Lung inflammation was observed in the inavolisib 4-week toxicology study in dogs at the highest dose tested. This finding was observed only at a dose level considered not tolerable in this species. Interstitial lung inflammation/pneumonitis has been observed in clinical studies with other PI3K inhibitors.

Immunosuppressant Effects. Immunosuppression and increased risk of infections are known to be associated with marketed PI3K/mTOR pathway inhibitors. Toxicology studies demonstrated decreases in reticulocytes, leukocytes, and absolute lymphocyte counts in animals treated with inavolisib. Patients who are immunocompromised as the result of HIV or receiving immunosuppressive therapies will be excluded. Patients will be monitored routinely for changes in circulating blood counts, including white cell differential, and should be monitored for fever and signs of infection.

Reproductive Effects. Potential adverse effects on male reproductive function, including focal inspissation of seminiferous tubule contents and multinucleated spermatids in the testis and epithelial degeneration/necrosis in the epididymis, were observed in one or more dogs in the 4-week repeat-dose toxicity study. Focal inspissation of seminiferous tubule contents persisted in one animal at the end of the 4-week recovery period.

Ocular Toxicities. In the 4-week toxicology study in rats, lens degeneration was observed in the highest inavolisib dose group (10 mg/kg; 4 of 30 rats). This finding was characterized by minimal-to-mild lens fiber swelling, separation of lens fibers, and/or accumulation of subcapsular proteinaceous material. It is unclear whether the lens finding was a direct effect of inavolisib or an indirect effect secondary to marked hyperglycemia in this dose group. No inavolisib-related eye findings were observed in rats at lower doses. In dogs, ocular-related findings included inflammation and lens fiber swelling. In dogs administered inavolisib (treated with 1.5 mg/kg and reduced to 1.0 mg/kg) for 3 months, ocular inflammation was limited to focal, minimal neutrophilic infiltrates in the stroma of the corneal-limbal junction of the eye. In the 4-week study in dogs, neutrophilic infiltration in limbus and sclera, mild endophthalmitis, and low-grade uveitis were observed in the highest dose group (treated with 5 mg/kg and reduced to 3 mg/kg), a dose that was not considered tolerable. These findings were reversible and likely part of a systemic generalized inflammatory condition. In dogs administered ≥0.3 mg/kg inavolisib in the 3-month toxicity study, bilateral, reversible, very slight swelling of the fibers at the equatorial region of the lens was observed in one male and one female at 0.3 mg/kg, and one male and one female treated with 1.5 mg/kg and reduced to 1.0 mg/kg. Patients with any concurrent ocular or intraocular condition, such as cataract or diabetic retinopathy, that would require medical or surgical intervention will be excluded. In addition, patients with active uveitis or vitritis, history of uveitis, or active infectious process in the eye will also be excluded.

Treatment Interruption. If GDC-6036 is held for >21 days from the previous study treatment due to toxicity, the study treatment should not be re-initiated. GDC-6036 may be suspended for up to 21 days for unanticipated intercurrent medical events that are not associated with study treatment toxicity or disease progression.

Adverse Events. An adverse event as defined herein refers to any untoward medical occurrence in a clinical investigation subject administered an agent described herein in the combination therapies described herein, regardless of causal attribution. The terms "severe" and "serious" are not synonymous. Severity refers to the intensity of an adverse event (e.g., rated as mild, moderate, or severe, or according to NCI CTCAE); the event itself may be of relatively minor medical significance (such as severe headache without any further findings).

Adverse events to be monitored include nausea, vomiting, diarrhea, stomatitis, mucositis, hepatitis or elevation in ALT or AST, elevated bilirubin or clinical jaundice, systemic lupus erythematosus, nephritis, Events suggestive of hypersensitivity, infusion-mediated reactions, CRS, influenza-like illness, and systemic inflammatory response syndrome, atrial fibrillation, myocarditis, pericarditis, Vasculitis, Myositis, uveitis, retinitis, optic neuritis, autoimmune hemolytic anemia, Stevens-Johnson syndrome, dermatitis bullous, and toxic epidermal necrolysis.

Adverse events of special interest specific to inavolisib are as follows:
Grade ≥3 hyperglycemia
Grade ≥3 rash
Grade ≥3 diarrhea
Grade ≥2 pneumonitis
Grade ≥2 colitis or enterocolitis
Grade ≥3 stomatitis or mucosal inflammation
Grade ≥3 ALT or AST elevation Throughout this specification and the claims, the words "comprise," "comprises," and "comprising" are used in a non-exclusive sense, except where the context requires otherwise. It is understood that embodiments described herein include "consisting of" and/or "consisting essentially of" embodiments. It is further understood that recitation of "GDC-6036" as used herein refers to the freebase compound as well as the GDC-6036-adipate salt or other pharmaceutically acceptable salt thereof.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of treating lung cancer mediated by a $KRas^{G12C}$ mutation in a patient having such a lung cancer, the method comprising:
   (a) determining the absence or presence of a $KRas^{G12C}$ mutation in a sample taken from a patient with a suspected diagnosed cancer; and
   (b) where the patient sample comprises a $KRas^{G12C}$ mutation, administering to the patient an effective amount of a combination therapy comprising:

(1)

the adipate salt of GDC-6036 administered orally as a tablet or capsule QD at an amount of about 100 mg, 200 mg, or 400 mg according to a dosing regimen comprising one or more cycles; and (2)

inavolisib or a pharmaceutically acceptable salt thereof administered QD at an amount of about 3 mg, 6 mg, or 9 mg according to the dosing regimen comprising one or more cycles.

2. The method of claim 1, wherein the lung cancer is NSCLC.

3. The method of claim 1, wherein the lung cancer is adenocarcinoma, squamous-cell lung carcinoma or large-cell lung carcinoma.

4. The method of claim 1, wherein the dosing regimen comprises one or more 21-day cycles.

5. The method of claim 4, wherein the dosing regimen comprises a rest period wherein one or both of GDC-6036 and inavolisib is not administered.

6. The method of claim 1, wherein the dosing regimen comprises one or more 28-day cycles.

7. The method of claim 1, wherein GDC-6036 or a pharmaceutically acceptable salt thereof is administered at an amount of about 200 mg.

8. The method of claim 1, wherein GDC-6036 or a pharmaceutically acceptable salt thereof is administered at an amount of about 400 mg.

9. The method of claim 1, wherein inavolisib is administered at an amount of 6 mg.

10. The method of claim 1, wherein inavolisib is administered at an amount of 9 mg.

11. The method of claim 1, wherein the patient is not evaluated for the presence of mutant PIK3CA prior to administration.

12. A method of treating a solid tumor comprising a KRas$^{G12C}$ mutation in patient having such a cancer, said method comprising:
(a) determining the absence or presence of a KRas$^{G12C}$ mutation in a sample taken from a patient with a suspected diagnosed cancer;
(b) where the patient sample comprises a KRas$^{G12C}$ mutation, administering an effective amount of a combination therapy comprising:

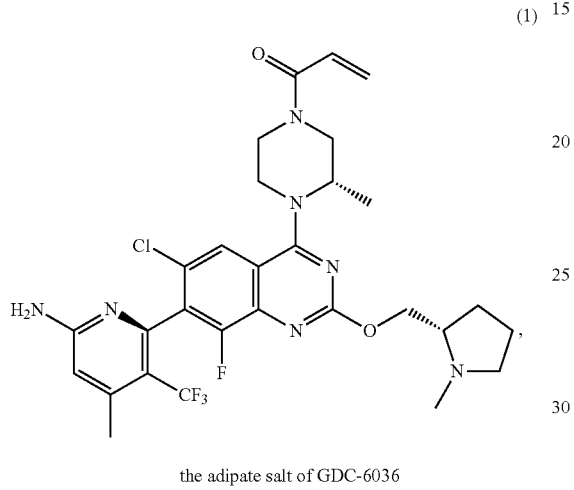

(1)

the adipate salt of GDC-6036 administered orally as a tablet or capsule QD at an amount of about 100 mg, 200 mg, or 400 mg according to a dosing regimen comprising one or more 21-day or 28-day cycles; and

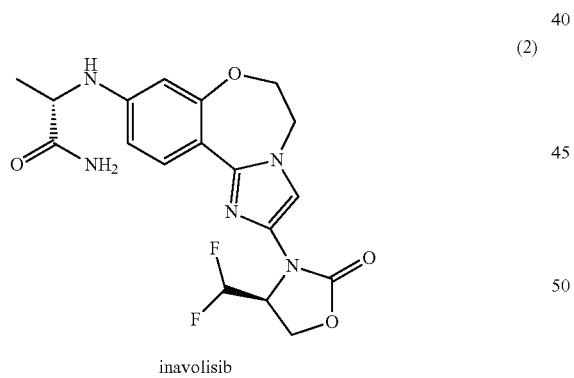

(2)

inavolisib or a pharmaceutically acceptable salt thereof is administered QD at an amount of about 3 mg, 6 mg, or 9 mg according to the dosing regimen comprising one or more 21-day or 28-day cycles; and
(c) wherein the patient is not evaluated for the presence of mutant PIK3CA prior to administration of the effective amount of the combination therapy of step (b).

13. The method of claim 12, wherein the solid tumor is colorectal cancer (CRC).

14. The method of claim 12, wherein GDC-6036 or a pharmaceutically acceptable salt thereof is administered at an amount of about 200 mg.

15. The method of claim 12, wherein GDC-6036 or a pharmaceutically acceptable salt thereof is administered at an amount of about 400 mg.

16. The method of claim 12, wherein inavolisib is administered at an amount of 6 mg or 9 mg.

17. A method of treating tissue agnostic cancer comprising a KRas$^{G12C}$ mutation in a patient having such a cancer, said method comprising:
(i) determining the absence or presence of a KRas$^{G12C}$ mutation in a sample taken from the patient with a suspected diagnosed cancer;
(ii) where the patient sample comprises a KRas$^{G12C}$ mutation, administering an effective amount of a combination therapy comprising:

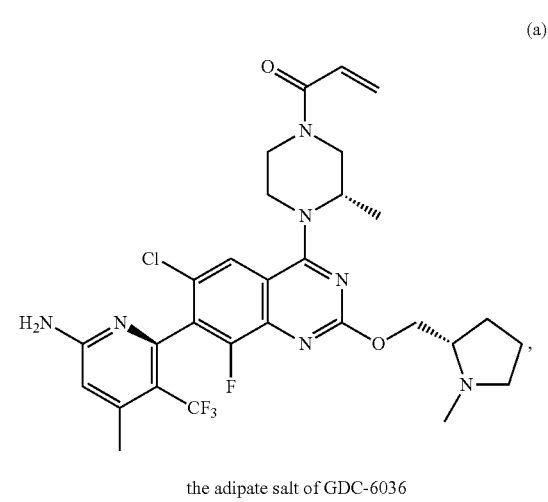

(a)

the adipate salt of GDC-6036 administered orally as a tablet or capsule QD at an amount of about 100 mg, 200 mg, or 400 mg according to a dosing regimen comprising one or more 21-day or 28-day cycles; and

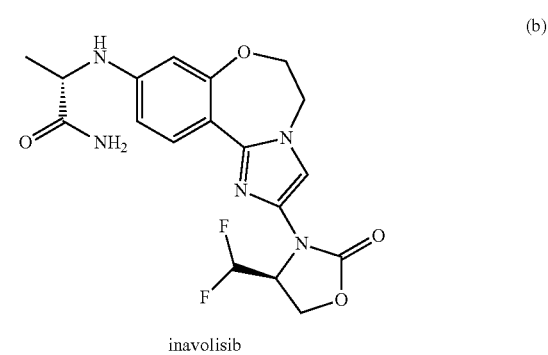 [SMILES: C[C@H](Nc1ccc2c(c1)OCCn1cc(N3C(=O)OC[C@H]3C(F)F)nc1-2)C(N)=O]

(b)

inavolisib or a pharmaceutically acceptable salt thereof is administered QD at an amount of about 3 mg, 6 mg, or 9 mg according to a dosing regimen comprising one or more 21-day or 28-day cycles; and
(iii) wherein the patient is not evaluated for the presence of mutant PIK3CA prior to administration.

18. The method of claim 17, wherein GDC-6036 or a pharmaceutically acceptable salt thereof is administered at an amount of about 100 mg, 200 mg, or 400 mg and inavolisib is administered at an amount of 6 mg or 9 mg.

* * * * *